(12) United States Patent
Lee et al.

(10) Patent No.: US 9,289,443 B2
(45) Date of Patent: Mar. 22, 2016

(54) PHARMACEUTICAL COMPOSITION AND METHOD FOR PREVENTING OR TREATING HEPATITIS C

(75) Inventors: Lain-Tze Lee, Hsinchu (TW);
Shau-Feng Chang, Hsinchu (TW);
Zong-Keng Kuo, Zhonghe (TW);
Hui-Ping Tsai, Hsinchu (TW)

(73) Assignee: INDUSTRIAL TECHNOLOGY RESEARCH INSTITUTE, Hsinchu County (TW)

( * ) Notice: Subject to any disclaimer, the term of this patent is extended or adjusted under 35 U.S.C. 154(b) by 344 days.

(21) Appl. No.: 13/281,441

(22) Filed: Oct. 26, 2011

(65) Prior Publication Data

US 2012/0165279 A1    Jun. 28, 2012

(30) Foreign Application Priority Data

Dec. 22, 2010 (TW) .............................. 99145165 A

(51) Int. Cl.
*A61K 31/704* (2006.01)

(52) U.S. Cl.
CPC .................................... *A61K 31/704* (2013.01)

(58) Field of Classification Search
None
See application file for complete search history.

(56) References Cited

FOREIGN PATENT DOCUMENTS

| CN | 101628021 A | | 1/2010 |
|---|---|---|---|
| JP | H4-005235 A | | 1/1992 |
| WO | WO99/07395 | * | 2/1999 |
| WO | 2006046674 A1 | | 5/2006 |

OTHER PUBLICATIONS

Peien et al., Shandong Medical Journal, vol. 33, No. 1, pp. 16-17, Dec. 31, 1993, English abstract only.*
Notice of First Examination opinion issued by the China Intellectual Property Office on Mar. 7, 2013, for the above-referenced application's counterpart application in China (Application No. 201110026354.X).
Pan Peien et al., "Discussion of the efficacy of different medications in hepatitis C.", Shandong Medical Journal, vol. 33, No. 1, pp. 16-17 (Dec. 31, 1993).
Office Action (Notification of Examination Opinion) issued by the Taiwan Intellectual Property Office on Nov. 27, 2012, for the above-referenced application's counterpart application in Taiwan (Application No. 99145165).
Ma et al., "HCV Protease Inhibitory, Cytotoxic and Apoptosis-Inducing Effects of Oleanolic Acid Derivatives", J Pharm Pharmaceut Sci, vol. 12, Issue: 2, pp. 243-248, Sep. 10, 2009.
Notice of Second Examination Opinion issued by China's State Intellectual Property Office on Oct. 10, 2013, for the above-referenced application's counterpart application in China (Application No. 201110026354.X).

* cited by examiner

*Primary Examiner* — Traviss C McIntosh, III
(74) *Attorney, Agent, or Firm* — Pai Patent & Trademark Law Firm; Chao-Chang David Pai

(57) ABSTRACT

A pharmaceutical composition for preventing or treating hepatitis C is provided, including oleanolic acid derivatives as an active ingredient and a pharmaceutically acceptable carrier. A method for preventing or treating hepatitis C in a subject in need thereof is also provided by administering the subject the pharmaceutical composition given above.

16 Claims, No Drawings

US 9,289,443 B2

PHARMACEUTICAL COMPOSITION AND METHOD FOR PREVENTING OR TREATING HEPATITIS C

CROSS REFERENCE TO RELATED APPLICATIONS

This application claims the priority of Taiwan Patent Application No. 099145165, filed Dec. 22, 2010, the entirety of which is incorporated by reference herein.

BACKGROUND

1. Technical Field

The disclosure relates to oleanolic acid derivatives as an active ingredient for prevention or treatment of hepatitis C, and in particular relates to the oleanolic acid derivatives containing a saccharide group as an active ingredient for prevention or treatment of hepatitis C.

2. Description of the Related Art

Hepatitis C is an infectious disease caused by the Hepatitis C virus (HCV) through drug injection or contaminated blood products, resulting in hepatitis combinations, such as jaundice, decreased appetite, fatigue, abdominal pain or abnormal liver function. An estimated 3% of people worldwide (about 3 millions) are infected with hepatitis C (according to WHO), but most have few symptoms at the early stage without diagnoses. About 20% of people recover from the disease by self-clearing the virus after infection. Up to 80% of persons develop chronic hepatitis, in which 20% result in cirrhosis.

Current treatment uses conventional and long-effect interferon and ribavirin to control chronic viral hepatitis. It is known that the treatment of interferon shows bad response rates following continuous administration and drug-resistance and also causes severe side effects, such as retinopathy, thyroiditis, acute pancreatitis, depression, etc. A combination of interferon and ribavirin has been used but the side effects are not decreased. There is a need for new drugs useful in the prevention or treatment of hepatitis C infection with few side effects.

There is a need to develop novel compounds for the prevention and treatment of hepatitis C infection.

SUMMARY

One embodiment of the present invention provides a pharmaceutical composition for preventing or treating hepatitis C, comprising oleanolic acid derivatives as an active ingredient and a pharmaceutically acceptable carrier.

The oleanolic acid derivative comprises a compound represented by the following Formula (I) or a stereoisomer thereof,

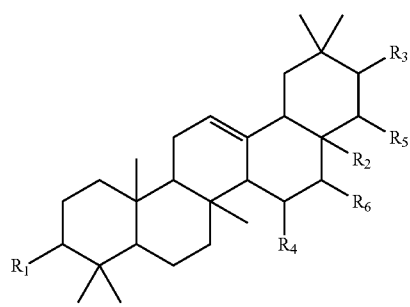

(I)

wherein $R_1$ represents a hydroxyl group or an unsubstituted or substituted saccharide group; $R_2$ represents a hydrogen atom, carboxylic acid, carbonyl, carboxy, alkoxycarbonyl, hydroxymethyl group or an unsubstituted or substituted saccharide group; $R_3$ represents a hydrogen atom, hydroxyl, carboxy, alkylcarboxy, alkenylcarboxy group or an unsubstituted or substituted saccharide group; $R_4$ represents a hydrogen atom, hydroxyl, alkyl, alkylcarboxy, or alkenylcarboxy group; $R_5$ represents a hydrogen atom, hydroxyl, alkylcarboxy, alkenylcarboxy or phenylcarboxy group; and $R_6$ represents a hydrogen atom, hydroxyl, carbonyl, carboxy or alkylcarboxy group.

One embodiment of the present invention also provides a method for prevention or treatment of hepatitis C in a subject in need thereof, comprising administering the subject the pharmaceutical composition given above.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The "oleanolic acid derivative" herein refers to a compound derived from a chemical structure of an oleanolic acid. Specifically, the oleanolic acid derivative according to embodiments of the present invention comprises a compound represented by the following Formula (I):

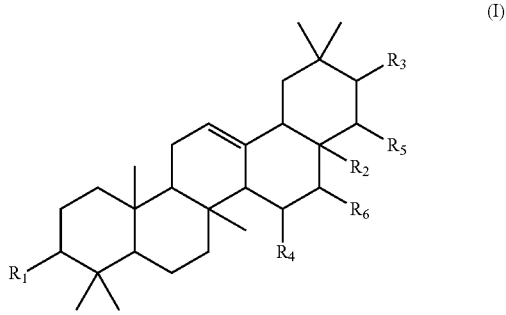

(I)

wherein $R_1$ represents a hydroxyl group or an unsubstituted or substituted saccharide group; $R_2$ represents a hydrogen atom, carboxylic acid, carbonyl, carboxy, alkoxycarbonyl, hydroxymethyl group or an unsubstituted or substituted saccharide group; $R_3$ represents a hydrogen atom, hydroxyl, carboxy, alkylcarboxy, alkenylcarboxy group or an unsubstituted or substituted saccharide group; $R_4$ represents a hydrogen atom, hydroxyl, alkyl, alkylcarboxy, or alkenylcarboxy group; $R_5$ represents a hydrogen atom, hydroxyl, alkylcarboxy, alkenylcarboxy or phenylcarboxy group; and $R_6$ represents a hydrogen atom, hydroxyl, carbonyl, carboxy or alkylcarboxy group.

The compound represented by the Formula (I) might have a different orientation of the functional groups within a molecule and therefore form stereoisomers, such as optical isomers, racemates, enantiomers, etc. Accordingly, the present invention includes the stereoisomers of the compound represented by the Formula (I).

The functional group recited herein is accordant with the definition conventionally used in the art. More specific, the "hydroxyl" refers to a functional group containing an oxygen atom bound covalently with a hydrogen atom, usually represented as —OH. The "carbonyl" refers to a functional group consisting of a carbon atom double-bonded to an oxygen atom, also written as "—CO". The "carbonyloxy" refers to a functional group consisting of a carbonyl group linked with an oxy group (—O—), which can be shown as "—$CO_2$". The "carboxylic acid" refers to a functional group consisting of a carbonyl and a hydroxyl, usually written as —COOH. The "phenylcarbonyloxy" refers to a functional group containing a carbonyloxy group with a substitution of a phenyl group.

The "alkyl" recited herein refers to a functional group consisting only of carbon atoms and hydrogen atoms linked by single bonds with linear or branched chains, usually represented by a general formula $C_nH_{2n+1}$. The alkyl group recited in the present invention specifically comprises a $C_1$~$C_{12}$ alkyl group consisting of 1~12 carbon atoms and preferably comprises a $C_1$~$C_6$ alkyl group consisting of 1~6 carbon atoms.

The "alcohol group" recited herein refers to a hydroxyl group bonded to a carbon atom. The alcohol group recited in the present invention specifically comprises 1~3 hydroxyl groups of a $C_1$~$C_{12}$ alkyl group.

The "alkoxy" herein refers to an alkyl group singularly bonded to an oxygen atom, also shown as a general formula "R—O". The "alkoxycarbonyl" herein refers to a carbonyl group with a substitution of an alkoxy group. The alkoxycarbonyl group recited herein specifically comprises a $C_1$~$C_{12}$ alkoxycarbonyl group and preferably comprises a $C_1$~$C_6$ alkoxycarbonyl group.

The "alkylcarboxy" herein refers to a carboxy group with a substitution of an alkyl group. More specific, the alkylcarboxy group according to the present invention comprises a $C_1$~$C_{12}$ alkylcarboxy group and preferably comprises a $C_1$~$C_6$ alkylcarboxy group.

The "alkenyl" herein refers to a functional group consisting only of carbon atoms and hydrogen atoms linked by at least one double bond with linear or branched chains, which is also shown as a general formula $C_nH_{2n}$. The "alkenylcarboxy" recited herein refers to a carboxy group with a substitution of an alkenyl group. The alkenylcarboxy group recited in the present invention specifically comprises a $C_2$~$C_{12}$ alkenylcarboxy group and preferably comprises a $C_2$~$C_6$ alkenylcarboxy group.

The "unsubstituted or substituted saccharide group" recited herein refers to a saccharide group with or without at least one substitution. The saccharide group is generally shown as $C_m(H_2O)_n$. The saccharide group recited in the present invention comprises a pentose consisting of 5 carbon atoms, a hexose consisting of 6 carbon atoms or a combination of one or more pentoses and hexoses. More specific, the pentose recited in the present invention comprises a furanose or pyranose, and the hexose herein comprises a rhamnose or glucose. Each of saccharide groups may be linked by a single bond, an oxy group (—O—), a thio group (—S—) or an amino group (—N—). The saccharide groups are preferably linked by a single bond or an oxy group (—O—). The saccharide group may be substituted by one or more groups, such as a hydroxyl, carbonyl, carboxy, alkyl, alkoxycarbonyl, alkenyl, alkenyloxycarbonyl or carboxyphenyl group. The alkyl group of the "alkyl" and "alkoxycarbonyl" herein comprise a $C_1$~$C_{12}$ alkyl group and preferably a $C_1$~$C_6$ alkyl group. The alkenyl group of the "alkenyl" and "alkenyloxycarbonyl" herein comprise a $C_2$~$C_{12}$ alkenyl group and preferably a $C_2$~$C_6$ alkenyl group.

In one embodiment, $R_1$ and $R_2$ of the Formula (I) respectively represent an oxy group bonded with 1~5 unsubstituted or substituted pentoses, hexoses or a combination thereof.

In another embodiment, $R_1$ of the Formula (I) represents a hydroxyl group bonded with 1~5 unsubstituted or substituted pentoses, hexoses or a combination thereof, and $R_4$ represents an alkenylcarboxy group.

More specific, the compound represented by the Formula (I) of embodiments of the present invention comprises the following embodiments:

(1) when $R_1$ represents a hydroxyl group bonded with one unsubstituted or substituted glucose and one unsubstituted or substituted pyranose, $R_2$ represents an carboxy group bonded with two unsubstituted or substituted pyranoses and one unsubstituted or substituted rhamnose;

(2) when $R_1$ represents a hydroxyl group bonded with two unsubstituted or substituted glucoses and three unsubstituted or substituted pyranoses, $R_2$ represents an carboxy group bonded with one unsubstituted or substituted glucose, one unsubstituted or substituted pyranose and one unsubstituted or substituted furanose;

(3) when $R_1$ represents a hydroxyl group bonded with two unsubstituted or substituted glucoses and one unsubstituted or substituted pyranose, $R_2$ represents an carboxy group bonded with two unsubstituted or substituted glucoses and three unsubstituted or substituted pyranoses;

(4) when $R_1$ represents a hydroxyl group bonded with one unsubstituted or substituted glucose and one unsubstituted or substituted pyranose, $R_2$ represents an carboxy group bonded with two unsubstituted or substituted rhamnoses and one unsubstituted or substituted pyranose;

(5) when $R_1$ represents a hydroxyl group bonded with one unsubstituted or substituted rhamnose, one unsubstituted or substituted pyranose and two unsubstituted or substituted glucoses, $R_2$ represents a hydroxymethyl group;

(6) when $R_1$ represents a hydroxyl group bonded with one unsubstituted or substituted rhamnose, one unsubstituted or substituted pyranose and two unsubstituted or substituted glucoses, $R_2$ represents a hydroxymethyl group and $R_4$ represents an alkenylcarboxy group;

(7) when $R_1$ represents a hydroxyl group bonded with two unsubstituted or substituted pyranoses and two unsubstituted or substituted glucoses, $R_2$ represents an carboxy group bonded with one unsubstituted or substituted furanose, one unsubstituted or substituted pyranose and two unsubstituted or substituted glucoses;

(8) when $R_1$ represents a hydroxyl group bonded with two unsubstituted or substituted pyranoses and two unsubstituted or substituted glucoses, $R_2$ represents an carboxy group bonded with three unsubstituted or substituted pyranoses and one unsubstituted or substituted glucose;

(9) when $R_1$ represents a hydrooxyl group bonded with two unsubstituted or substituted pyranoses and one unsubstituted or substituted glucose, $R_2$ represents an carboxy group bonded with two unsubstituted or substituted pyranoses, one unsubstituted or substituted glucose and two unsubstituted or substituted rhamnoses;

(10) when $R_1$ represents a hydroxyl group bonded with one unsubstituted or substituted pyranose and two unsubstituted or substituted glucoses, $R_2$ represents an carboxy group bonded with one unsubstituted or substituted pyranose, two unsubstituted or substituted glucoses and one unsubstituted or substituted rhamnose;

(11) when $R_1$ represents a hydroxyl group bonded with two unsubstituted or substituted pyranoses and one unsubstituted or substituted glucose, $R_2$ represents an carboxy group bonded with two unsubstituted or substituted pyranoses, one unsubstituted or substituted glucose and one unsubstituted or substituted rhamnose;

(12) when $R_1$ represents a hydroxyl group bonded with two unsubstituted or substituted pyranoses and one unsubstituted or substituted glucose, $R_2$ represents an carboxy group bonded with two unsubstituted or substituted pyranoses and two unsubstituted or substituted glucoses; and

(13) when $R_1$ represents a hydroxyl group bonded with one unsubstituted or substituted pyranose and two unsubstituted or substituted glucoses, $R_2$ represents an carboxy group bonded with one unsubstituted or substituted pyranose, two unsubstituted or substituted glucoses and one unsubstituted or substituted rhamnose.

The oleanolic acid derivative of embodiments of the present invention more specifically comprises compounds represented by the following formulas.

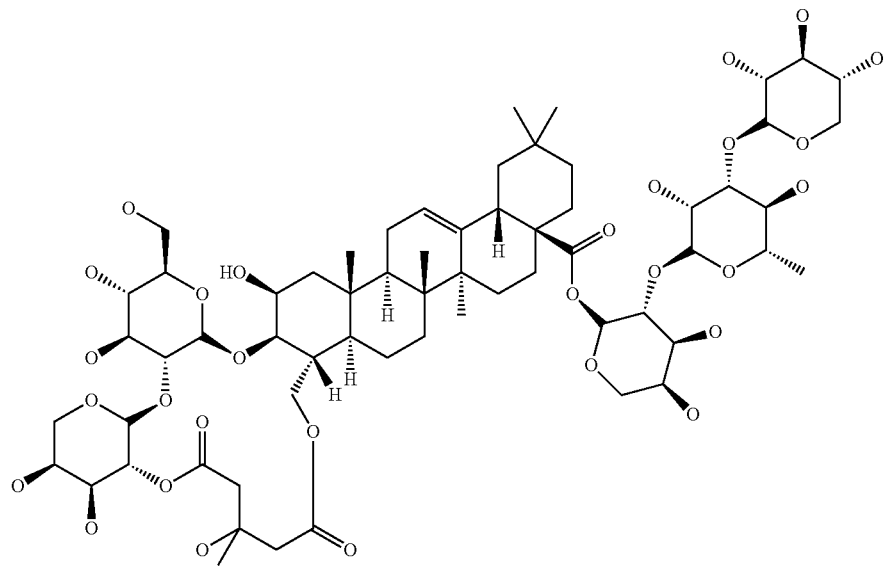

(A2)

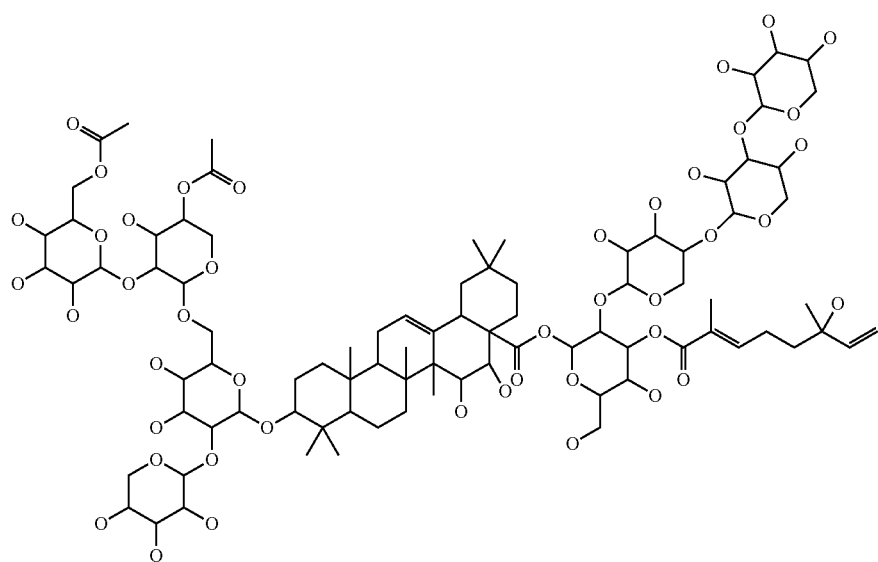

(A20)

-continued
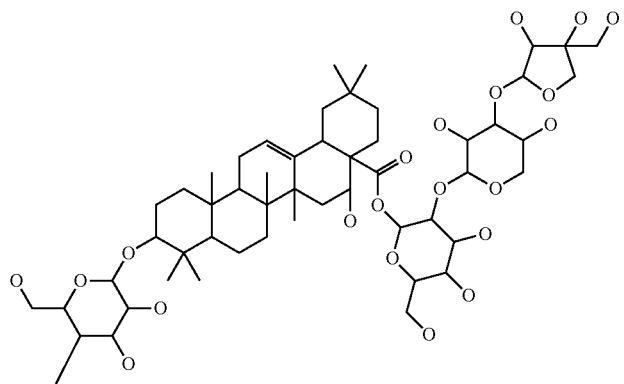
(A6)
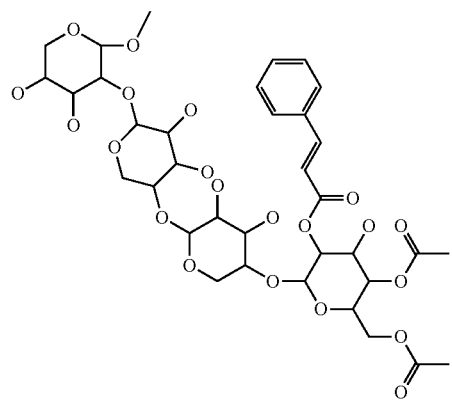
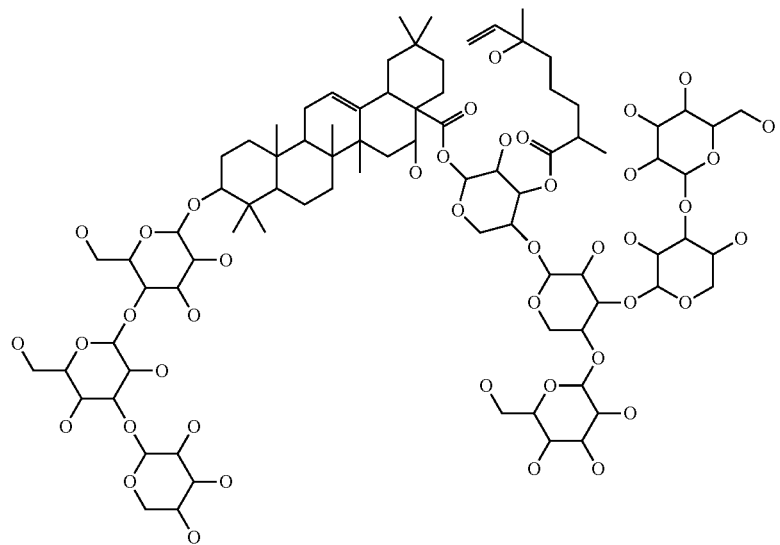
(A10)

-continued
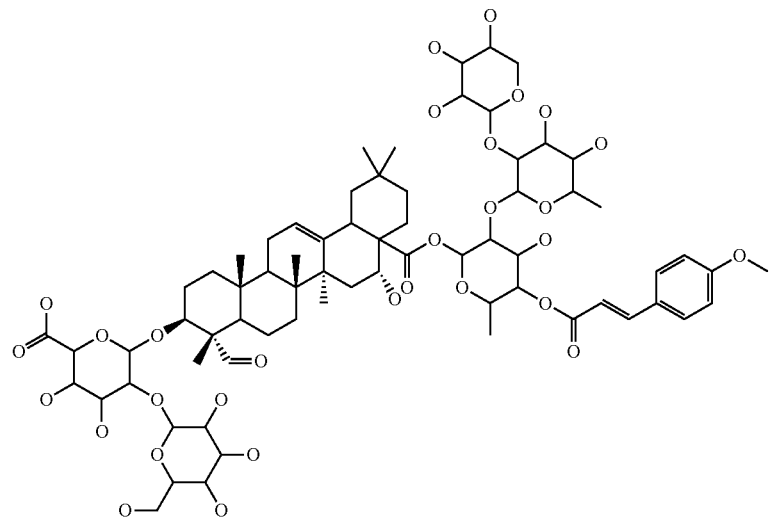
(A12)
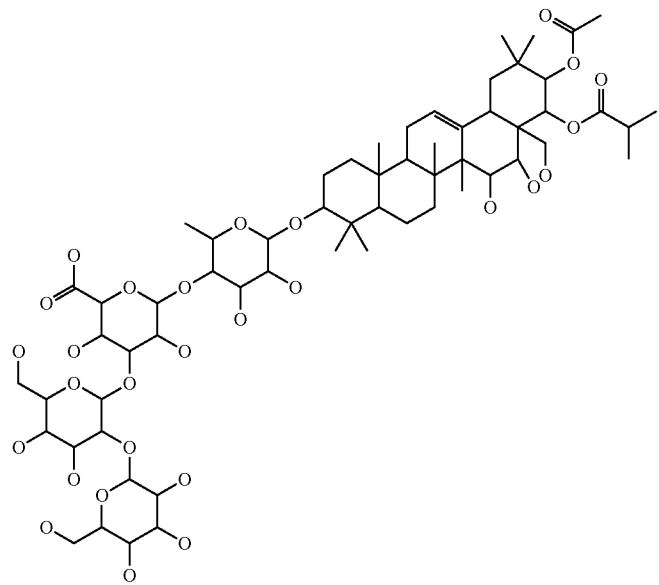
(A13)

-continued
(A14)
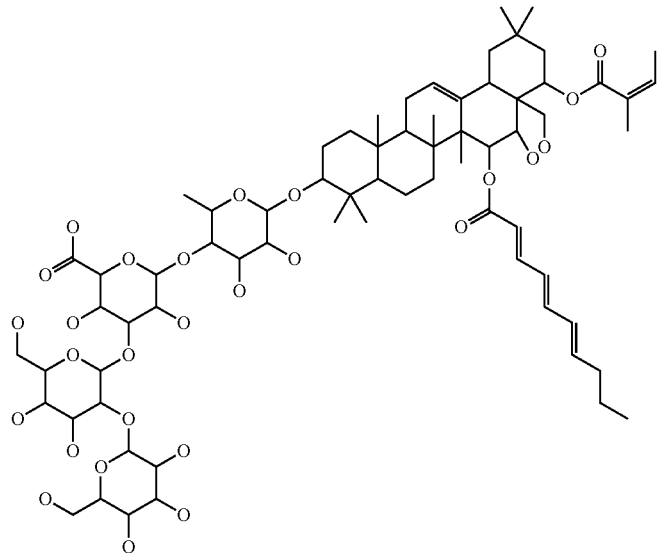
(A15)
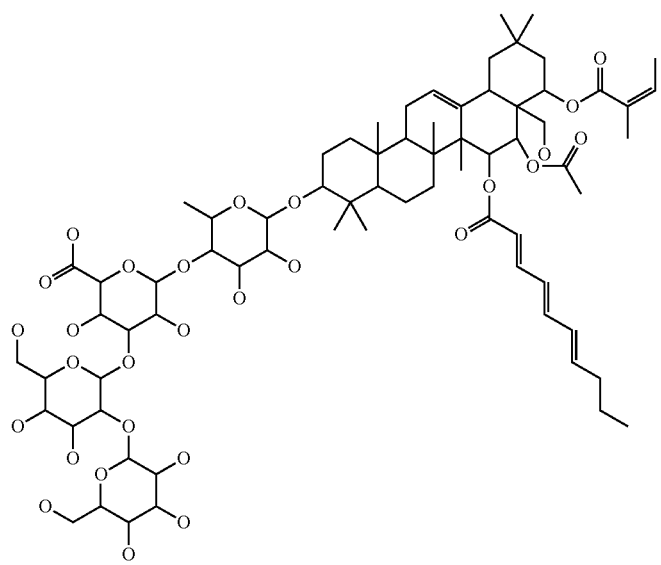
(A16)
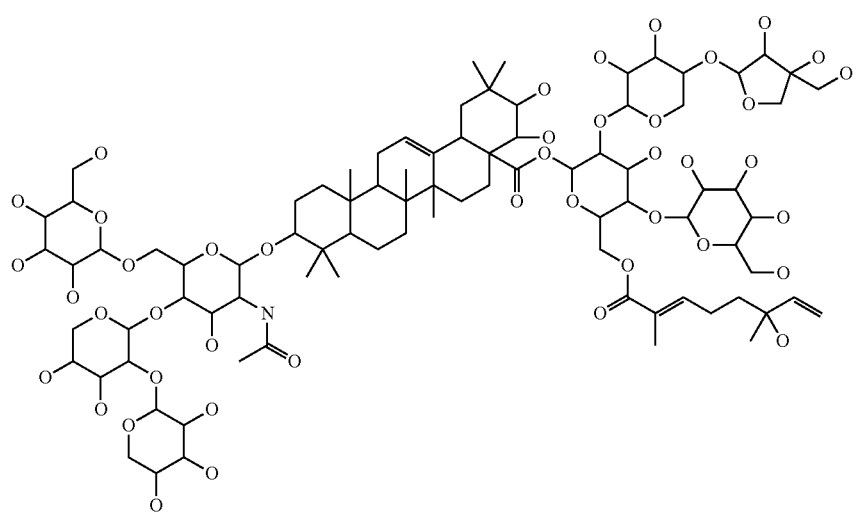

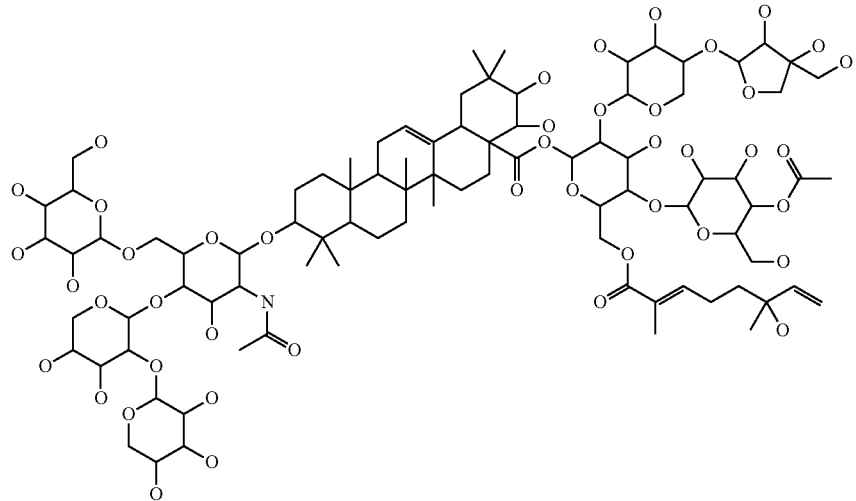
(A17)
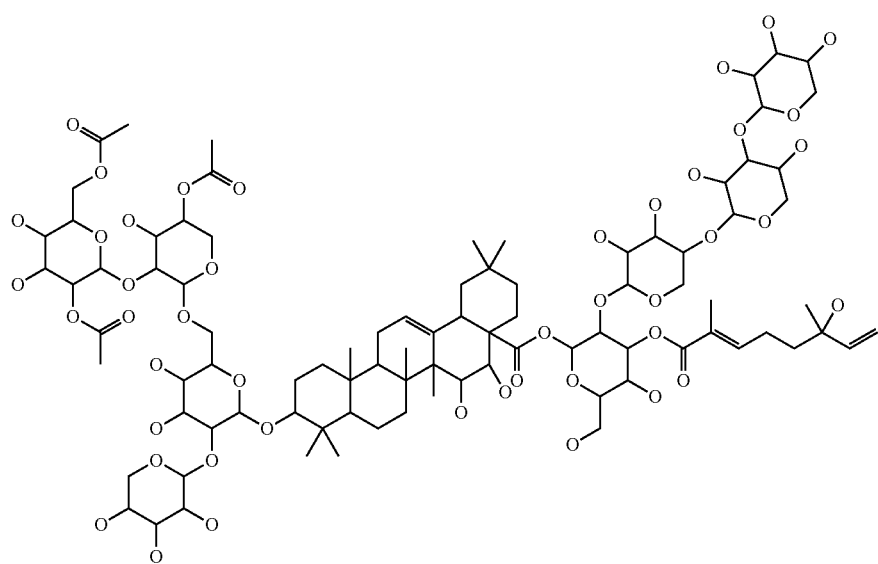
(A19)

-continued
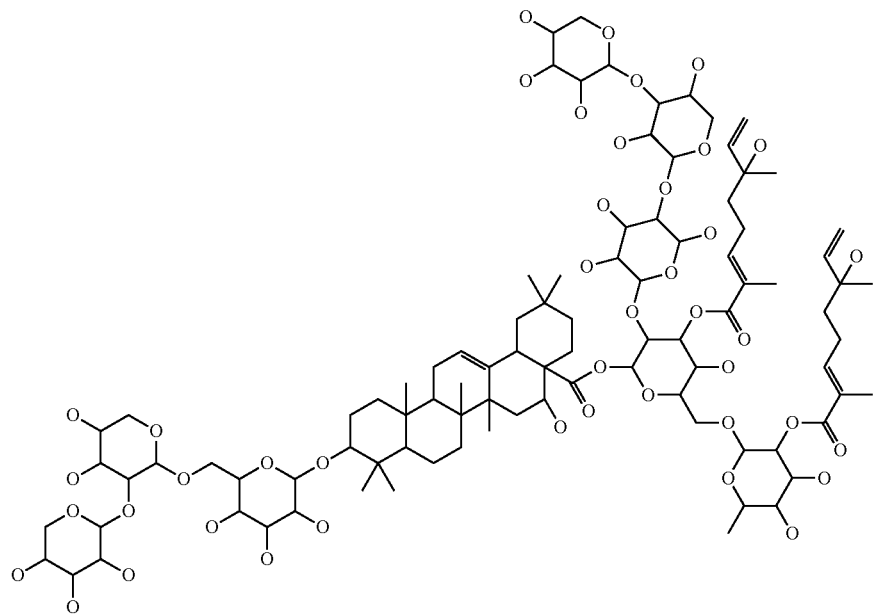
(A21)
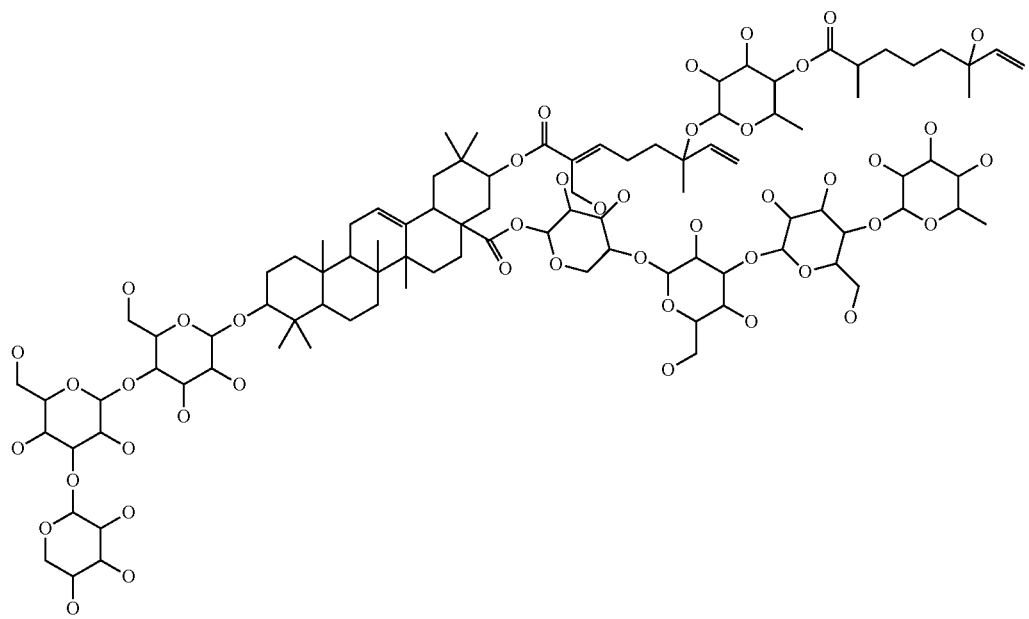
(A23)

-continued
(A25)
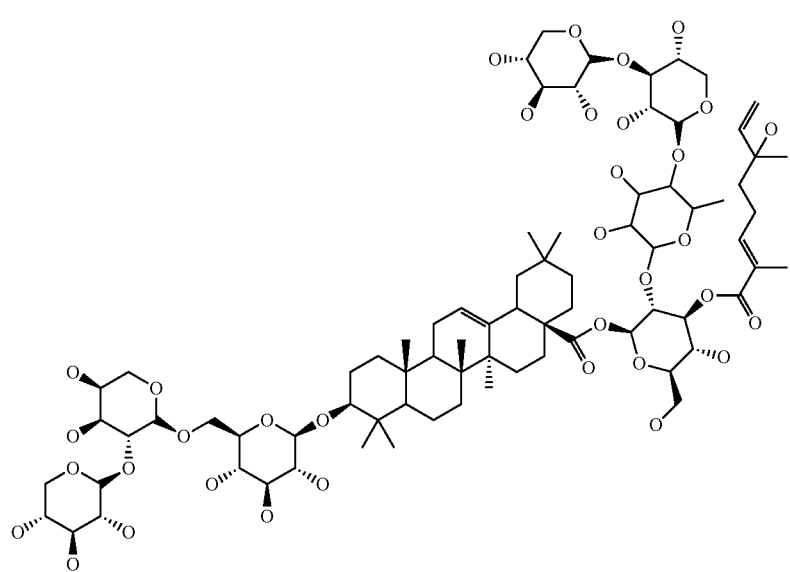
(A26)

-continued (A27)

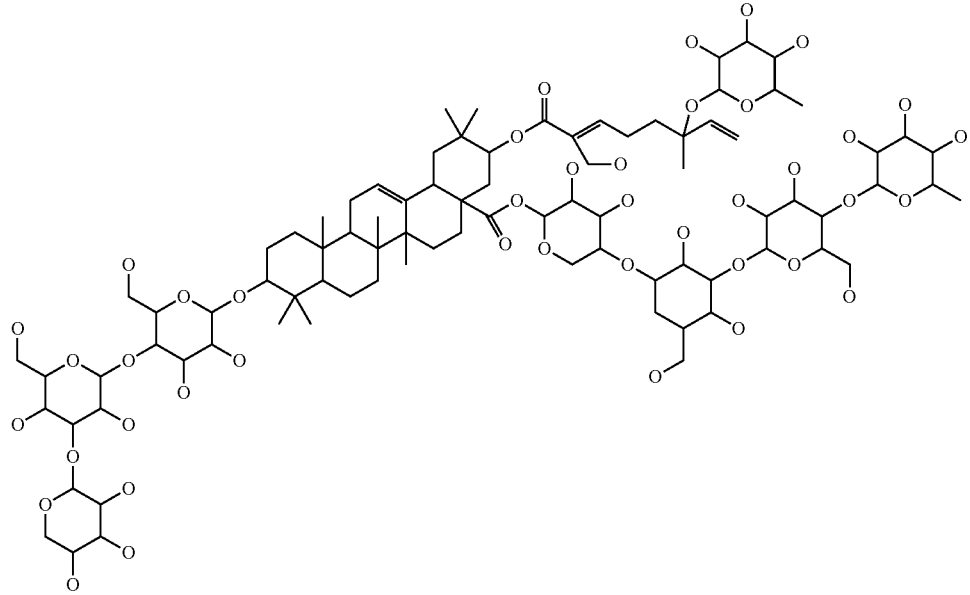

The compounds recited herein may be in a form of salts or stereoisomers. The salts or stereoisomers of the compounds which have bioactivity for the prevention or treatment of hepatitis C are all encompassed in the scope of the present invention. The salts may include sodium salts, potassium salts, amine salts, carboxylates, sulfates, nitrates, phosphates, silicates, and amino acid salts, etc. The stereoisomer may comprise optical isomers, racemates, enantiomers, or the like.

The compounds recited herein may be obtained from plant extracts or commercially available products. It has been known that oleanolic acid derivatives are used for anti-inflammatory modulating agents (Taiwan Patent Publication No. 201004626A1) or for the treatment or prevention of cancers, neuropathy, inflammatory disease and oxidation-related diseases (Taiwan Patent Publication No. 201004627A1). There is no publication disclosing the use and effect of oleanolic acid derivatives for the treatment and prevention of hepatitis C.

HCV replicon system was used to test the effects of compounds on the treatment and prevention of hepatitis C. The HCV replicon system has been acknowledged as a screening tool for new drugs (Lohmann, V. et al., 1999, Replication of subgenomic hepatitis C virus RNAs in hepatoma cell line, *Science*. Vol. 285, 110-113; Bartenschlager, R. 2002, Hepatitis C virus replicons: potential role for drug development, *Nature Reviews/Drug Discovery*. Vol. 1, 911-916; Vorlijk, J. M. et al., 2003, A replicon-based bioassay for the measurement of interferons in patients with chronic hepatitis C, *Journal of Virological Methods*. 110:201-209). The HCV replicon system includes a Huh-luc/neo-ET cell carrying I389luc-ubi-NS3-3'/ET gene construct which monitors the replicative capability of the HCV. In the HCV replicon system, a firefly luciferase-ubiquitin-neomycin fusion protein is expressed by the translation of the internal ribosomal entry site (IRES) of the HCV, and the hepatitis C viral nonstructural proteins (NS3-5B), which includes protease, helicase and polymerase, are expressed by the translation of the IRES of the encephalomyocarditis virus (EMCV).

The IRES of the hepatitis C virus or the hepatitis C viral nonstructural proteins consist of a replication complex. When the replication complex is affected by the candidate compound, the activity of the HCV replicon system is inhibited and the activity of the luciferase is reduced. Accordingly, the inhibition of the HCV can be estimated by determining the activity of the intensity of the luciferase expressed by the Huh-luc/noe-ET cell.

The "pharmaceutically acceptable carrier" or "acceptable carrier" herein refers to an excipient or additive accepted in the medicine or food industry. The excipient or additive may comprise starch, corn starch, gelatin, gum arabic, edible pigments, flavors, antioxidants or antiseptics. The pharmaceutical composition of the present invention can be administrated orally, transdermally, intraperitoneally, intravenously, nasally or intravitreally, in which oral administration is preferable.

The dosage of the pharmaceutical composition can be determined by the practitioners according to a patient's age, weight, health condition, disease type, disease development, affected parts, etc. The pharmaceutical composition of the present invention may be individually administrated or administrated in a combination of other drugs. The regime can be appropriately adjusted according to the conventional routines practiced by the practitioners in the art.

EXAMPLES

Cell Cytotoxic Test on Huh-luc/noe-ET Cells

Huh-luc/neo-ET cells with a concentration of $2.5 \times 10^4$ cells/100 µl/well were seeded into a 96 well culture plate (Corning Incorporation COSTAR, 3599) and placed into a cell incubator for culturing.

The next day, the oleanolic acid derivatives as listed in the following Tables 1 and 2 were diluted with a DMEM culture medium to the concentrations of 28.73 µg/ml, 9.57 µg/ml, 3.19 µg/ml, 1.06 µg/ml, 0.35 µg/ml, 0.11 µg/ml, 0.039 µg/ml and 0.013 µg/ml, respectively, or diluted to the concentrations of 114.92 µg/ml, 38.33 µg/ml, 12.77 µg/ml, 4.25 µg/ml, 1.42 µg/ml, 0.46 µg/ml, 0.16 µg/ml and 0.057 µg/ml, respectively. The initial medium in the 96 well culture plate was sucked out by a vacuum pump (DOAT-704AA) without removing the cells. Then, the culture medium containing the oleanolic acid derivatives were added into the 96 well culture plate containing 100 µl/well of the cells as the experiment groups, while the untreated culture mediums were added to the cells as a control.

After a two-day culture, the medium was removed and each well containing cells was washed by 100 µl of 1×PBS (1 mM $KH_2PO_4$, 10 mM $Na_2HPO_4$, 137 mM NaCl, 2.7 mM KCl) twice. Precipitates were recorded and PBS was removed. 50 µl of the medium containing 0.5 mg/ml of MTT (Sigma, M2128) was added into each well of the 96 well culture plate. The 96 well culture plate was placed in a $CO_2$ culture incubator for 1 hour. Subsequently, 150 µl of DMSO (Riedel-de Haül, 60153) was added to each well of the 96 well culture plate and vortexed (KS shaker Type 670) to thoroughly mix the resulting purple precipitates. The 96 well culture plate was then placed in a continuous wave length microwell plate analysis system (Molecular Devices, SPECTRAMAX 190) to measure the absorbance of cells at a wavelength of 560 nm.

The average absorbance of the control was set as 100% of the cell survival rates (%) to calculate the cell survival rates (%) of the experiment groups with different concentrations of the oleanolic acid derivatives.

The cell survival rate was calculated by the following formula:

Absorbance of the experiment group/Absorbance of the control×100%

The data of the cell survival rates for all experiment groups were plotted on an x-y graph to see the distribution. A trend line was obtained. According to the trend line, as y was 50, the correspondent X represented 50% cell cytotoxic concentration ($CC_{50}$) and as y was 85, the correspondent X represented 15% cell cytotoxic concentration ($CC_{15}$). The results are shown in Table 2.

When the cell survival rates was greater than 85%, it indicated that the compounds at or less than the concentration (the concentration less than $CC_{15}$) was non-cytotoxic. The compounds at or less than the non-cytotoxic concentrations were selected to test for the firefly luciferase activity of Huh-luc/neo-ET cells as follows.

Inhibition of the HCV Replication by Determining the Firefly Luciferase Activity Huh-luc/neo-ET cells with a concentration of $2.5 \times 10^4$ cells/100 µl/well were seeded into a 96 well culture plate (Corning Incorporation COSTAR, 3599) and placed into a cell incubator for culturing.

The oleanolic acid derivatives as listed in Table 2 were co-cultured with Huh-luc/neo-ET cells for 2 days. The mediums were washed twice by 100 µl of 1×PBS (1 mM $KH_2PO_4$, 10 mM $Na_2HPO_4$, 137 mM NaCl, 2.7 mM KCl) and PBS was removed. 35 µl of 1× passive lysis buffer (Promega, E1941) was added to the cells and vortexed for 10 minutes to thoroughly lysis the cells.

30 µl/well of the cell suspension was then added to a 96 well white plate (NUNC, 236108) for the measurement of the luciferase activity. Subsequently, 40 µl/well of luminescence analysis buffer and 20 µl/well of luminescence substrate (1 mM D-Luciferin) were added into the 96 well white plates. The luciferase activity (Rlu/s) was measured by a microplate luminescence meter (Berthold, MPL4) immediately.

The luciferase activity of the control was set as a standard to calculate the inhibition rates (%) of HCV of the experiment groups. The inhibition rates was calculated by the following formula:

$$\frac{[(\text{luciferase activity of control group}) - (\text{luciferase activity of experiment group})]}{(\text{luciferase activity of control group})} \times 100\%$$

After the test compounds were serial diluted and the inhibition rates of the HCV replication were determined at different concentrations, the concentration at 50% inhibition of the HCV replication ($IC_{50}$) was calculated by grafit5 software (Erithacus Software).

For each experiment, 0.5 ng/ml and 0.1 ng/ml of the PEG IFN alpha-2a were used as positive controls for the $IC_{50}$ test. Meanwhile, 1 µg/ml of cyclosporine A (CsA) was also used as a positive control for the $IC_{50}$ test. The result is shown in Table 2.

TABLE 1

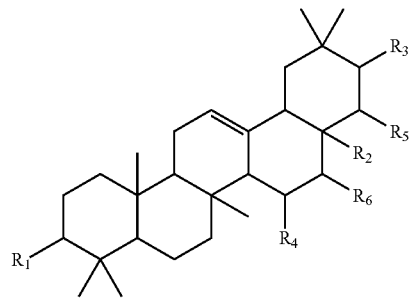

| No. | Compound |
|---|---|
| A01 | |

TABLE 1-continued
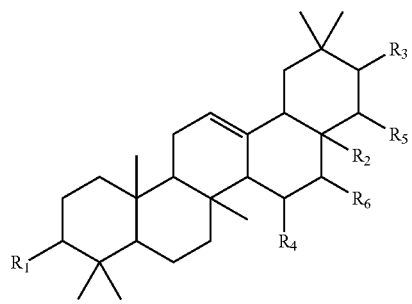
A02
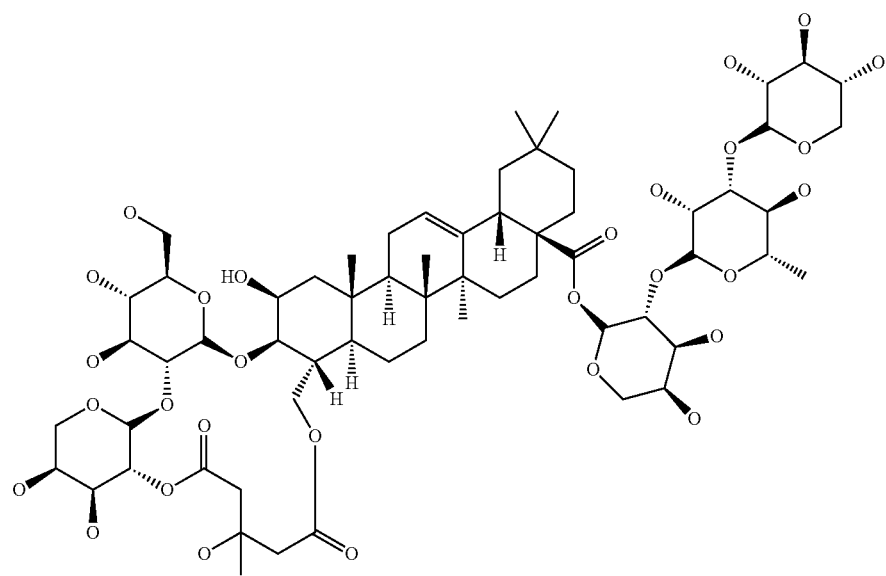
A03    Saikosaponin A
A04    Saikosaponin C
A05    Saikosaponin D
A06
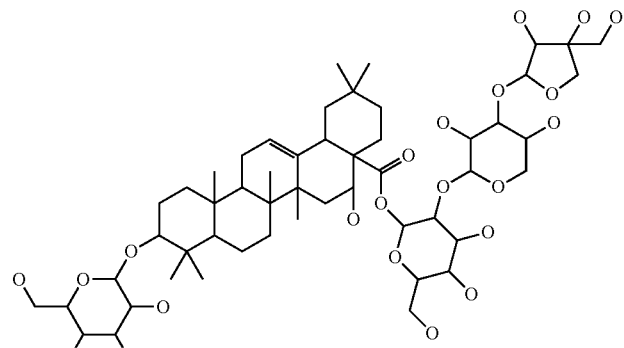

TABLE 1-continued
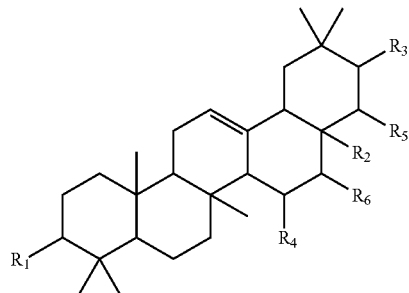
(I)
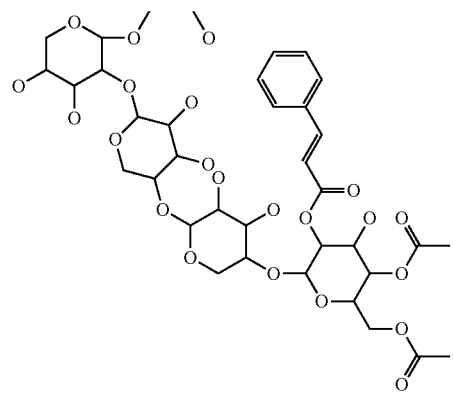
A07
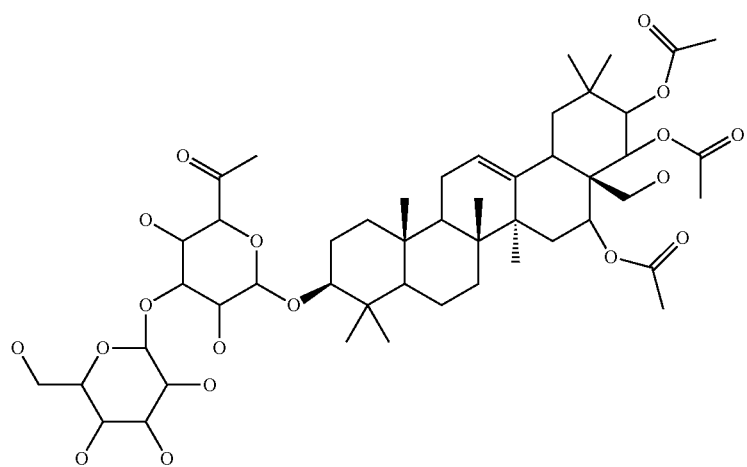
A08
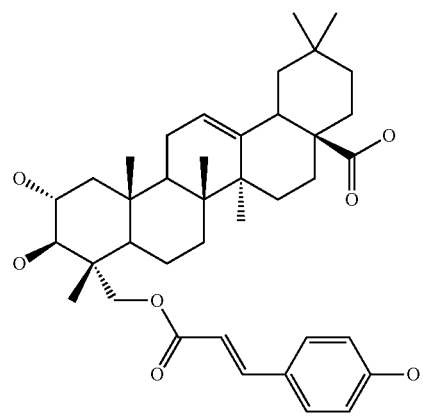

TABLE 1-continued
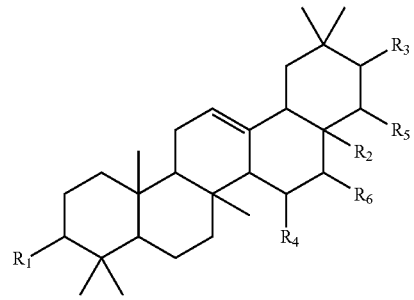
(I)
A09
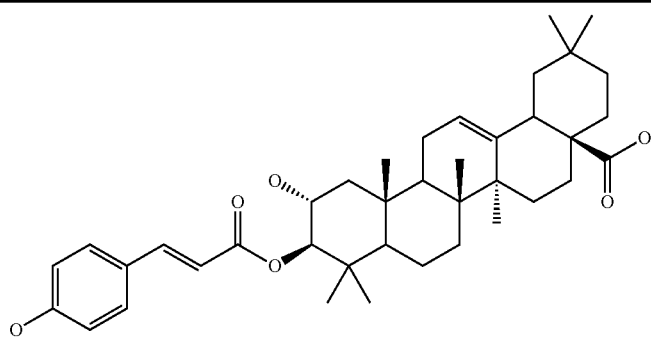
A10
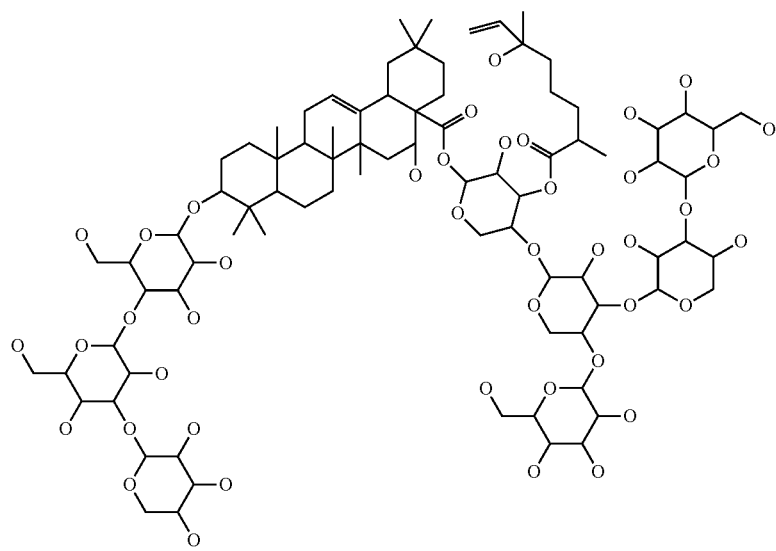
A11
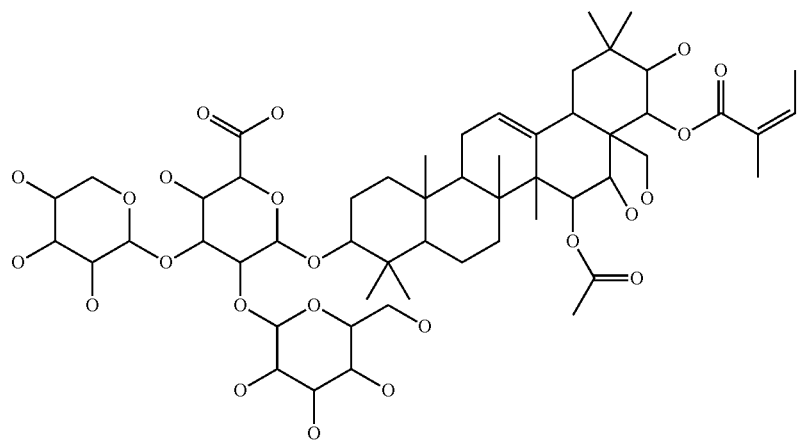

TABLE 1-continued
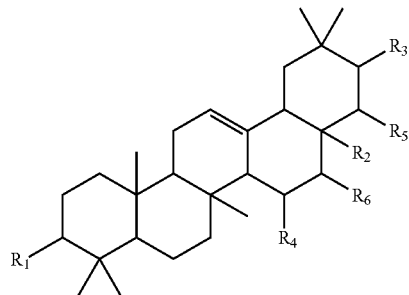
(I)
A12
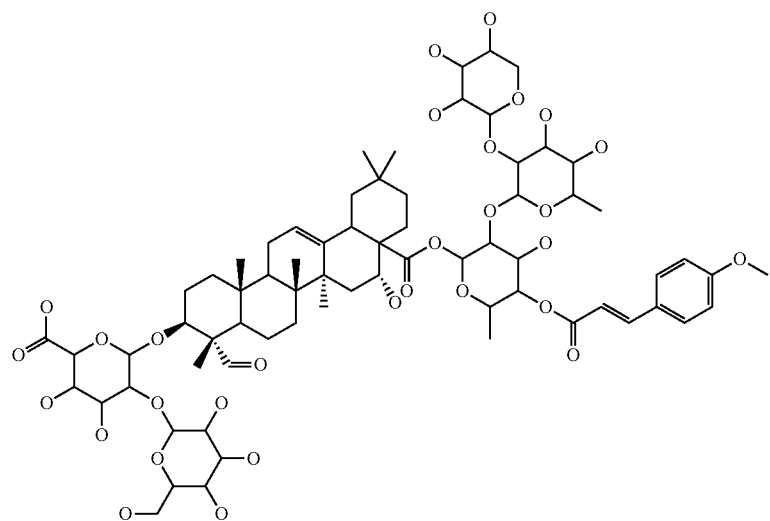
A13
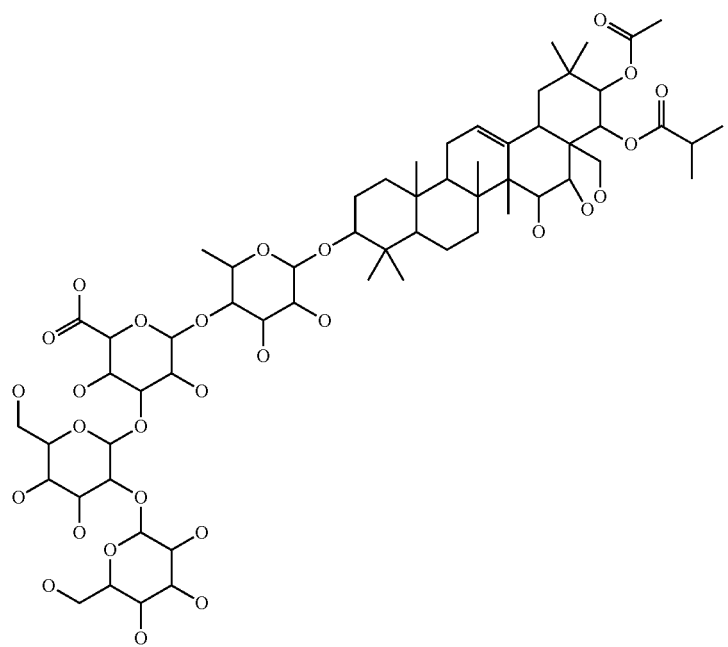

TABLE 1-continued
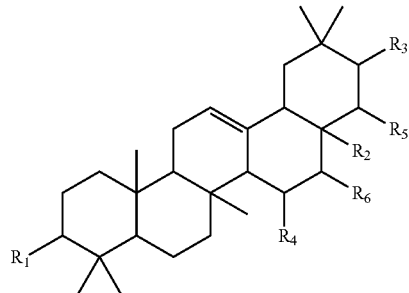
(I)
A14
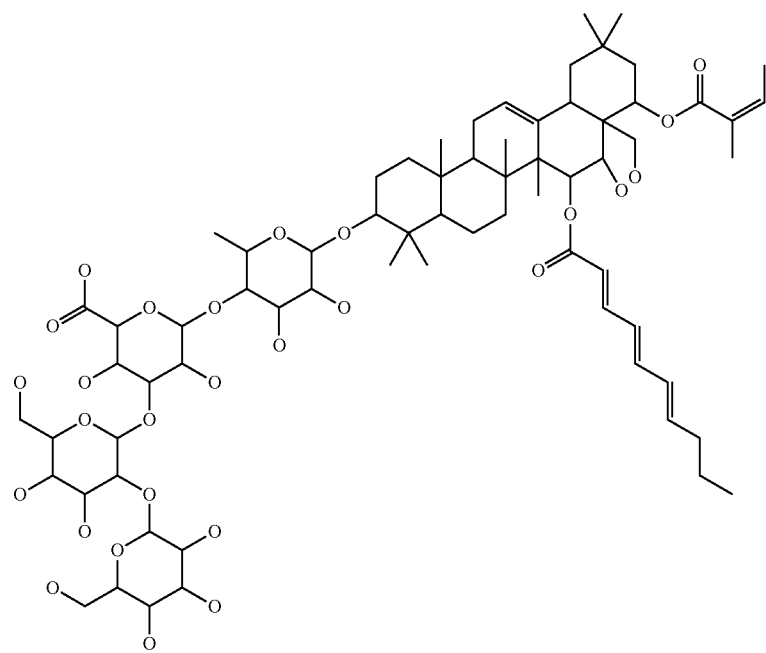
A15
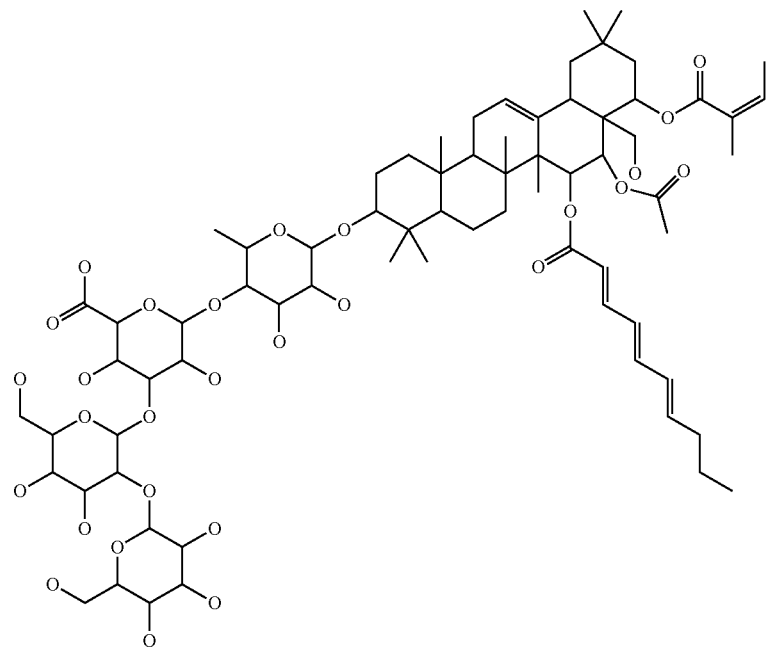

TABLE 1-continued
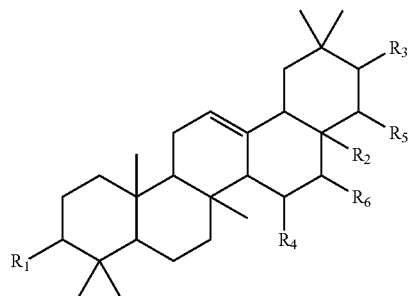
(I)
A16
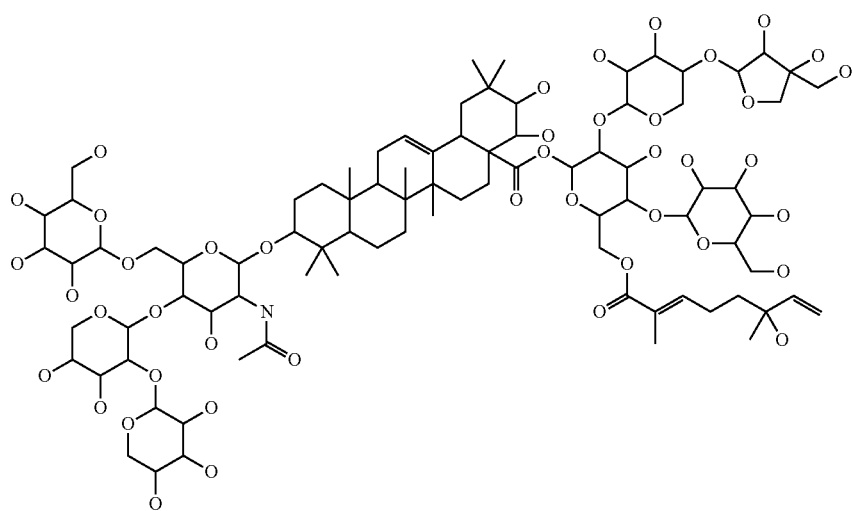
A17
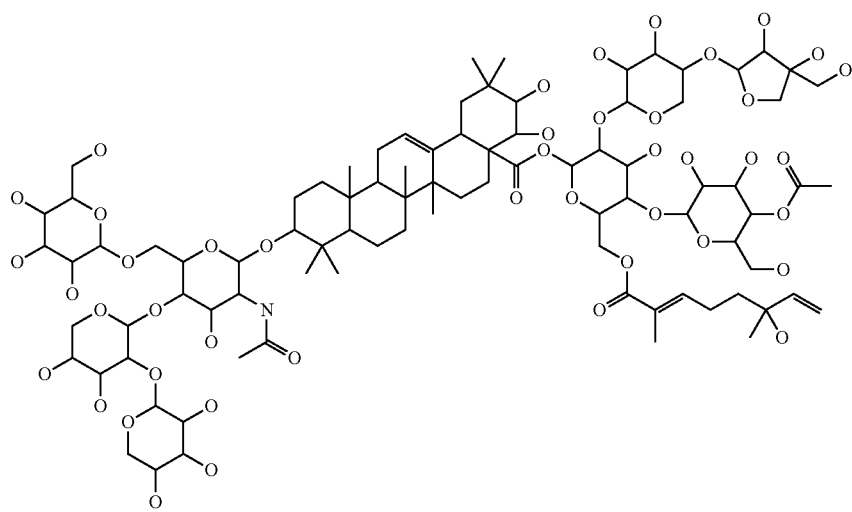

TABLE 1-continued
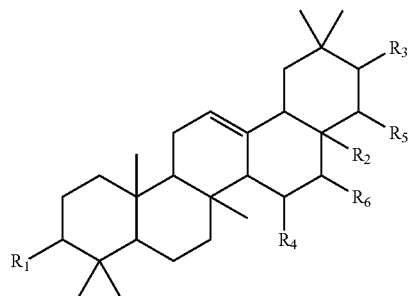
(I)
A18
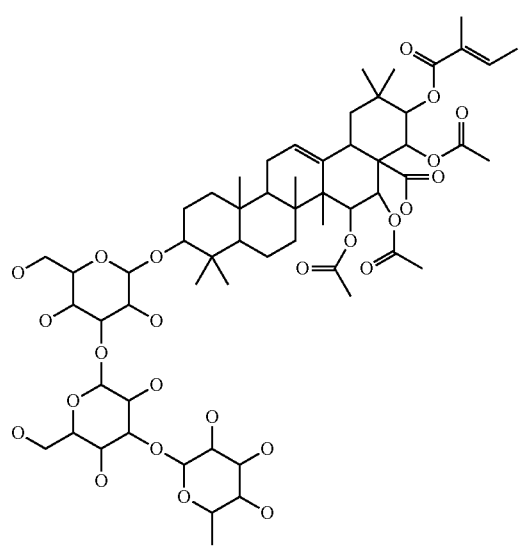
A19
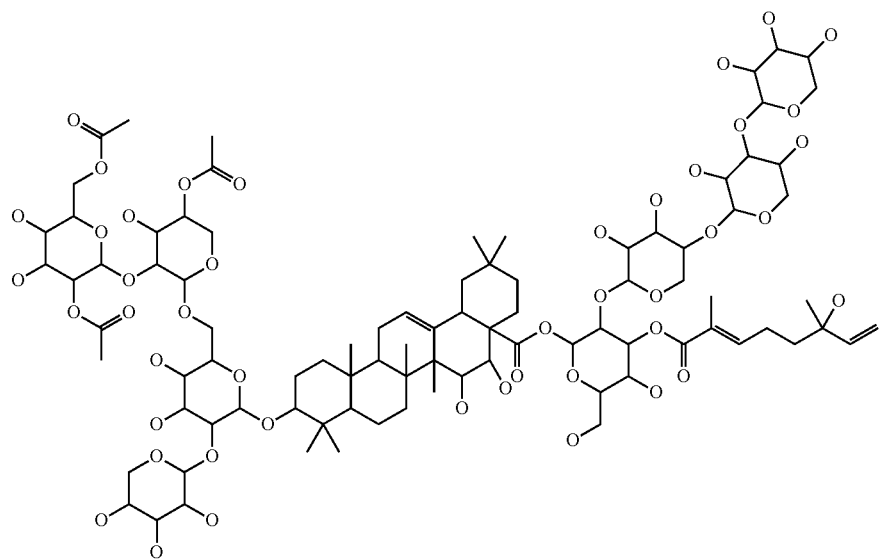

TABLE 1-continued
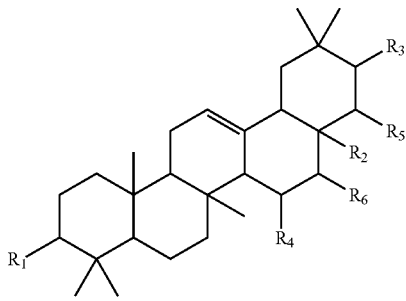
(I)
A20
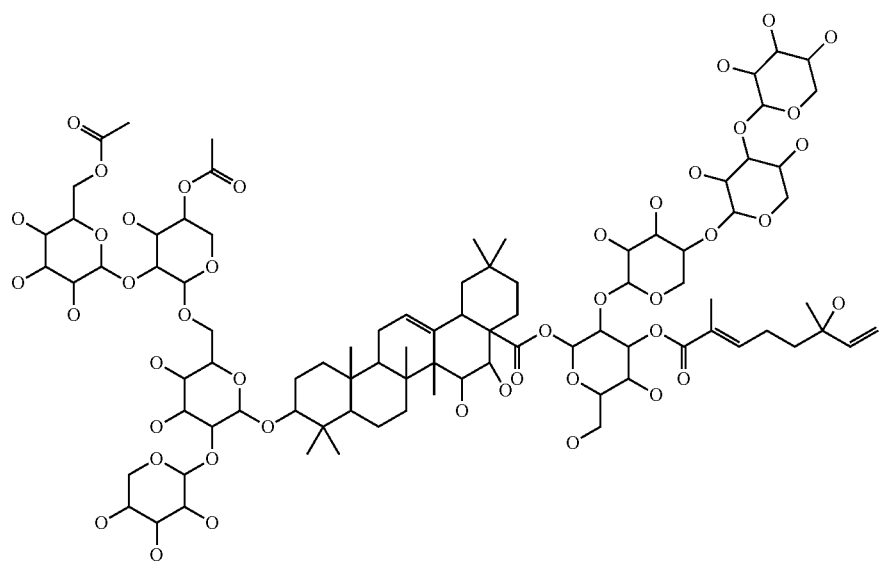
A21
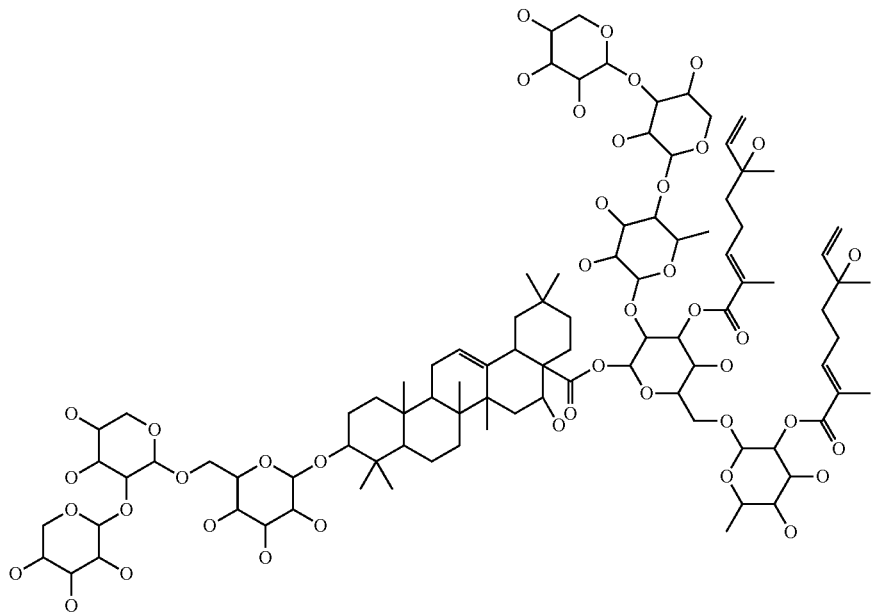

TABLE 1-continued
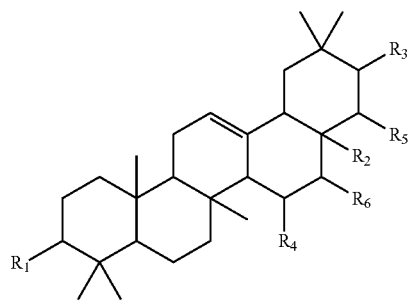
(I)
A22
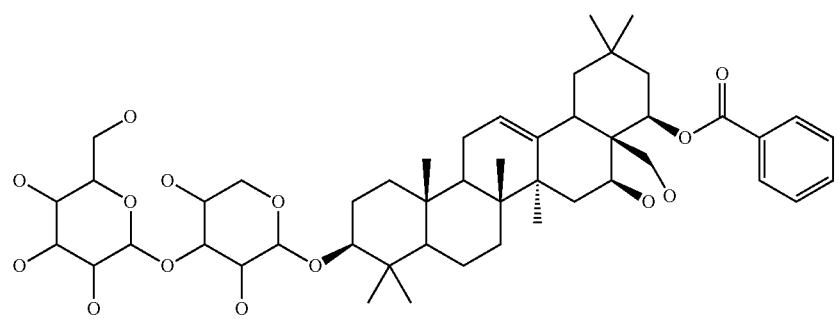
A23
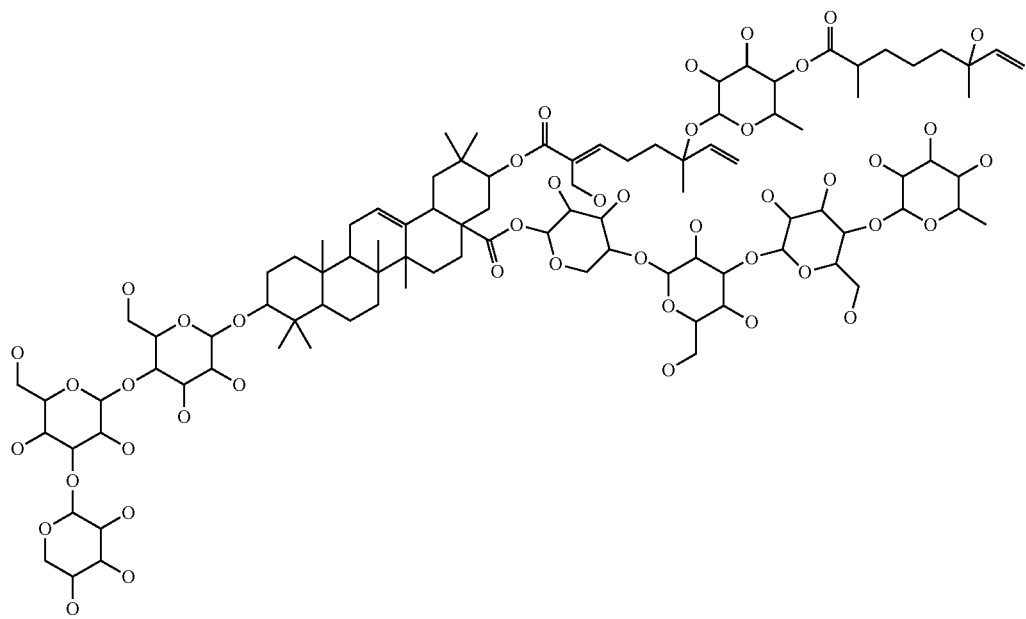

TABLE 1-continued
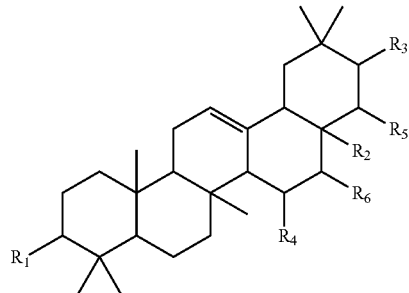
(I)
A24
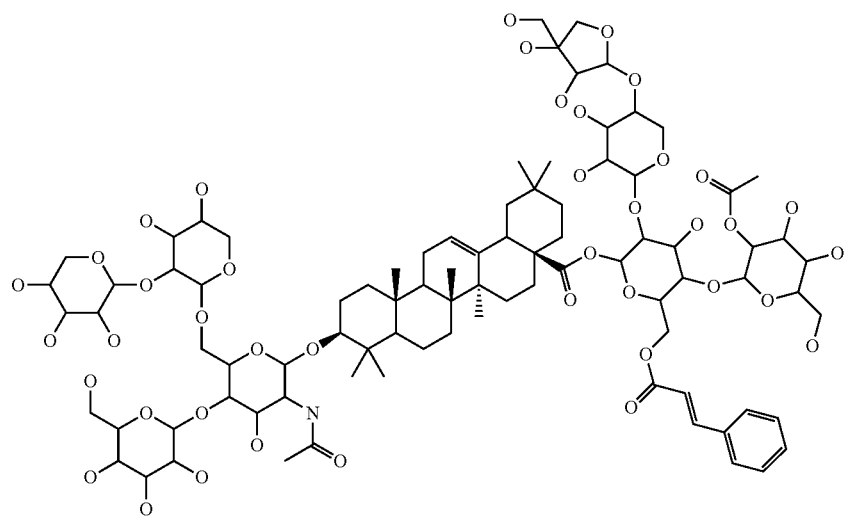
A25
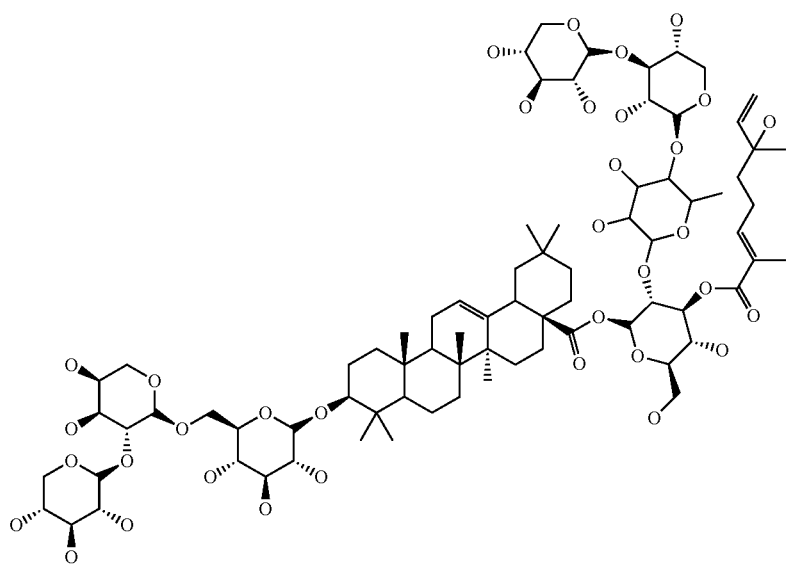

TABLE 1-continued
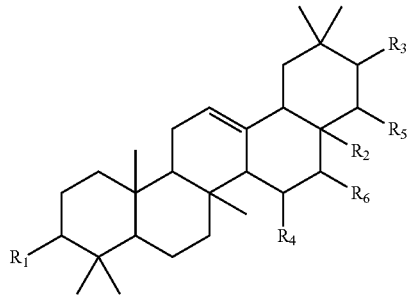
(I)
A26
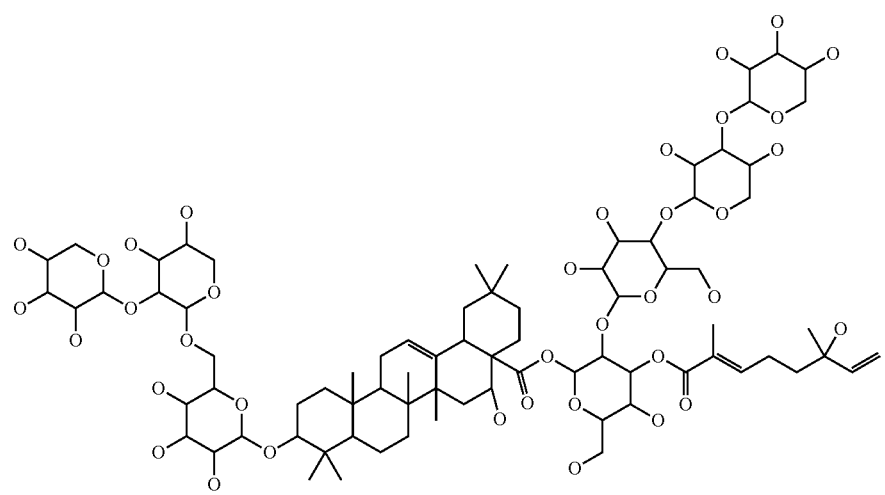
A27
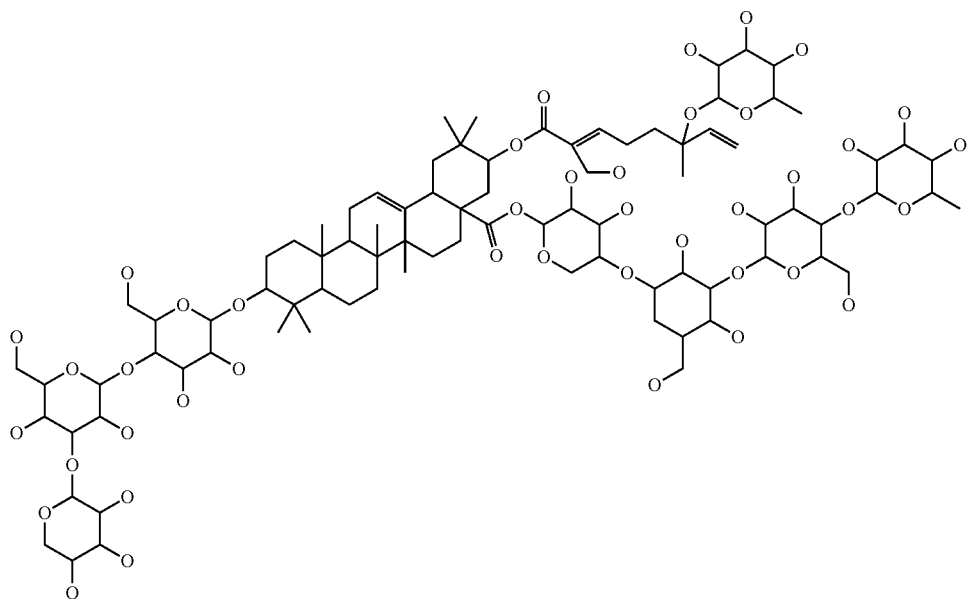
| No. | R₁ | R₂ |
| --- | --- | --- |
| A01 | OH | COOH |
| A02 | O-glc-pyr | —CO₂-pyr-rha-pyr |
| A03 | O-fur-glc | —CH₂O— |
| A04 | O-glc(-rha)-glc | —CH₂O— |
| A05 | O-fur-glc | —CH₂O— |

TABLE 1-continued
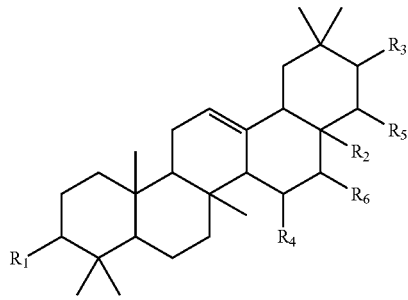
| A06 | 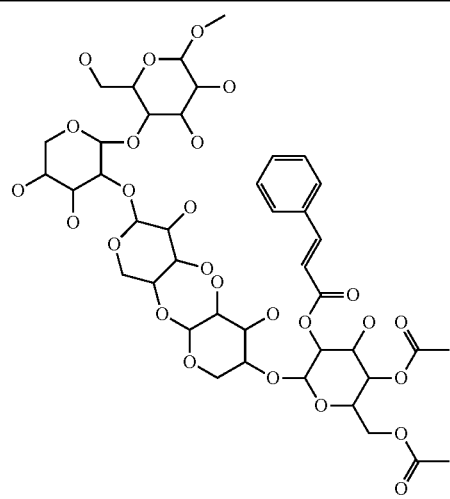 | 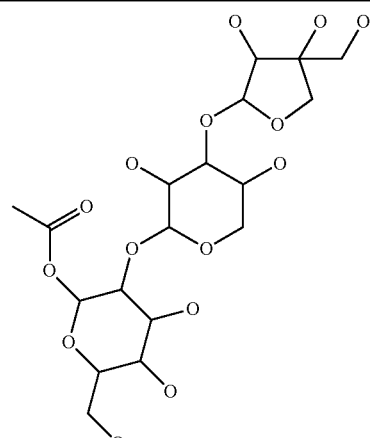 |
| --- | --- | --- |
| A07 | 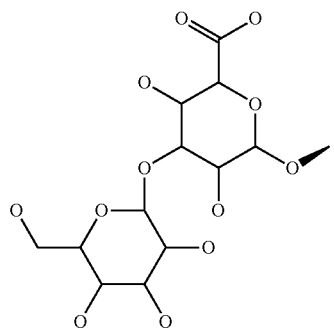 | —CH$_2$OH |
| A08 | —OH | —CO$_2$H |
| A09 | 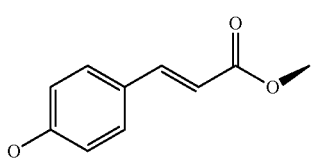 | —CO$_2$H |

TABLE 1-continued
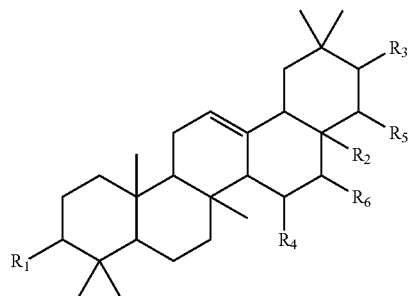
(I)
| | | | |
|---|---|---|---|
| A10 | —O-glc-glc-pyr | 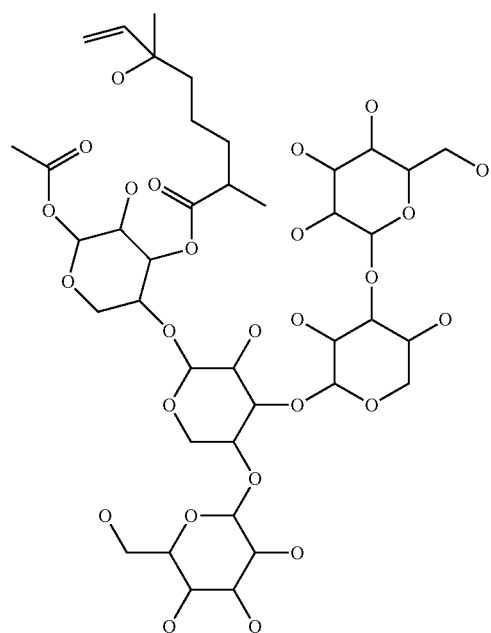 [SMILES: C=CC(C)(O)CCCC(C)C(=O)OC1C(OC2OCC(OC3OC(CO)C(O)C(O)C3O)C(OC3OCC(O)C(OC4OC(CO)C(O)C(O)C4O)C3O)C2O)COC(OC(C)=O)C1O] | |
| A11 | 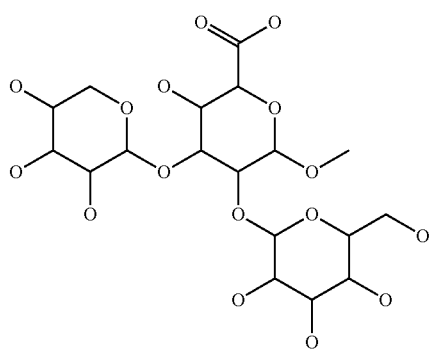 [SMILES: COC1OC(C(=O)O)C(O)C(OC2OCC(O)C(O)C2O)C1OC1OC(CO)C(O)C(O)C1O] | | —CH$_2$OH |

TABLE 1-continued
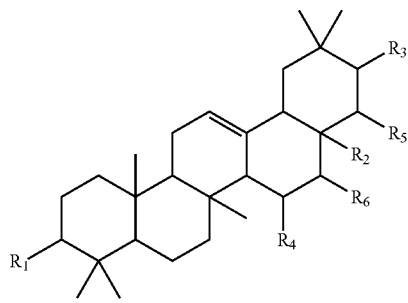
(I)
| | | |
|---|---|---|
| A12 | 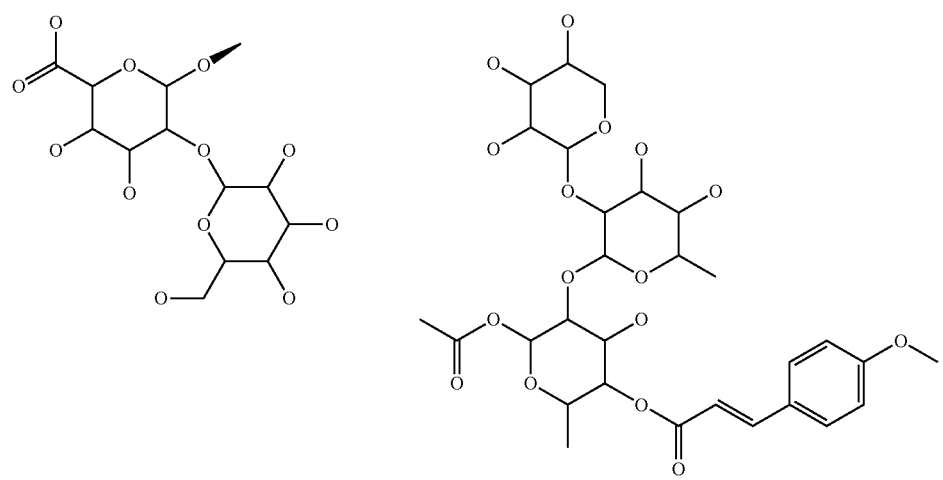 | —CH$_2$OH |
| A13 | 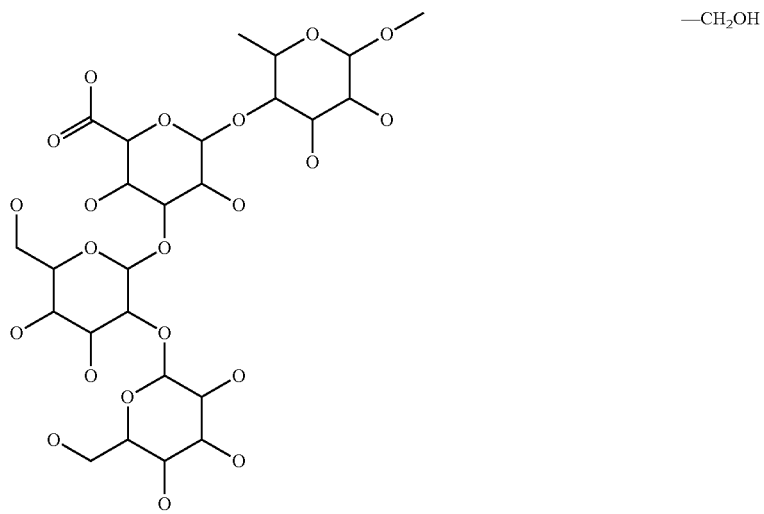 | |

TABLE 1-continued
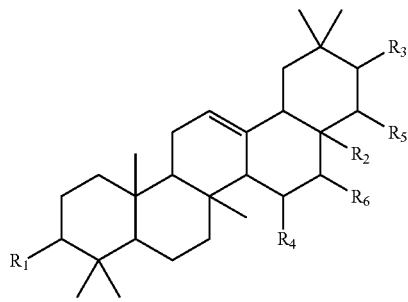
(I)
| A14 | 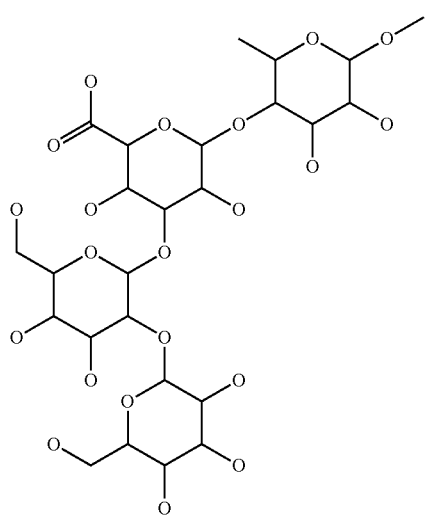 [SMILES: COC1OC(C)C(OC2OC(C(=O)O)C(O)C(OC3OC(CO)C(O)C(O)C3OC3OC(CO)C(O)C(O)C3O)C2O)C(O)C1O] | —CH₂OH |
| A15 | 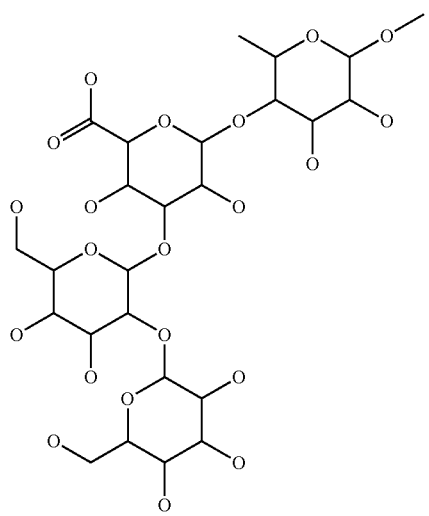 [SMILES: COC1OC(C)C(OC2OC(C(=O)O)C(O)C(OC3OC(CO)C(O)C(O)C3OC3OC(CO)C(O)C(O)C3O)C2O)C(O)C1O] | —CH₂OH |

TABLE 1-continued
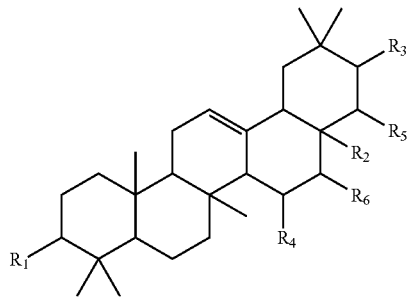
(I)
A16 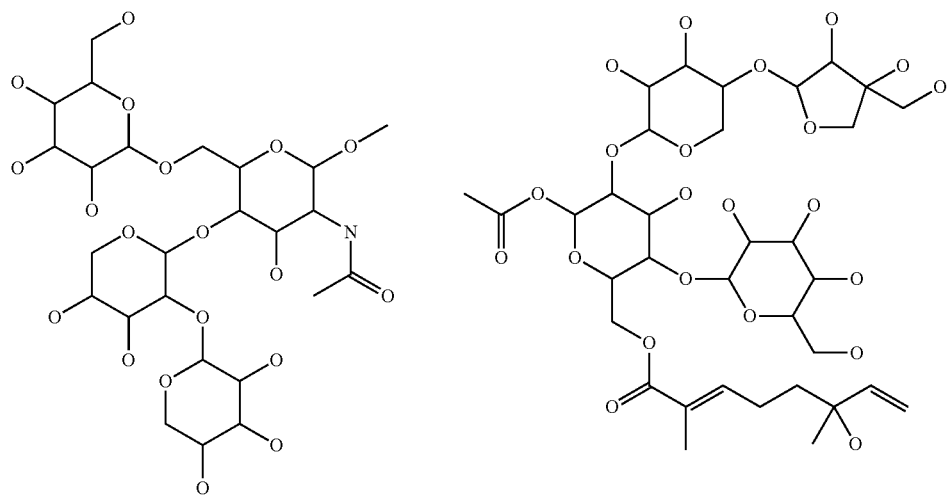
A17 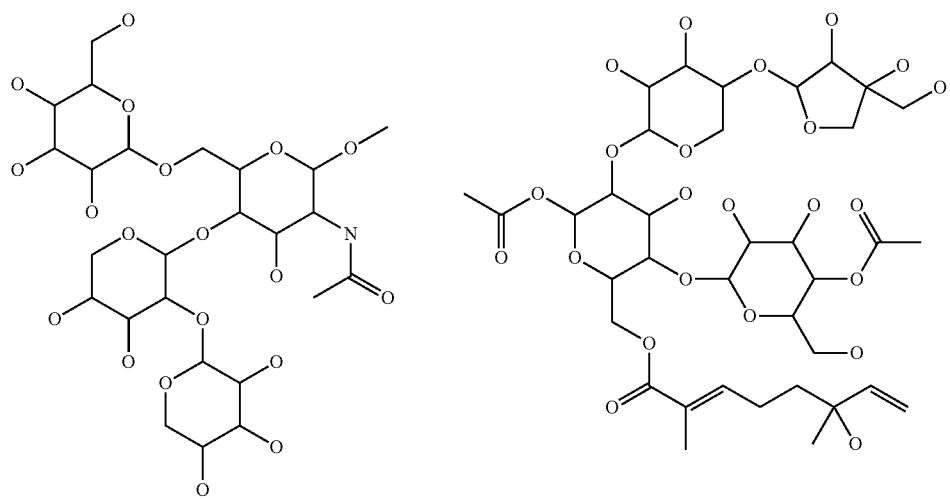
A18    —O-glc-glc-rha    —CO$_2$H TABLE 1-continued
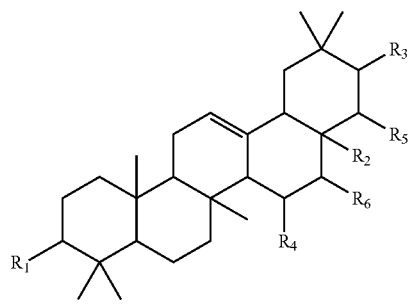
(I)
A19
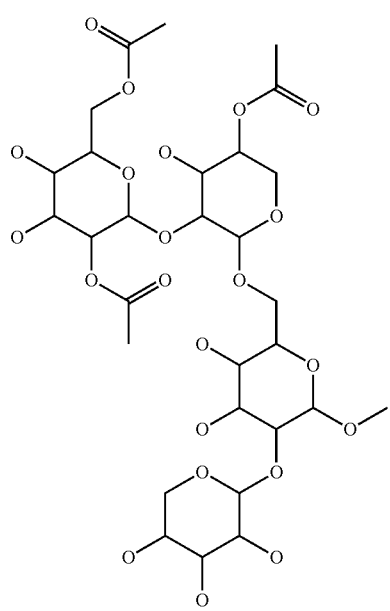 [SMILES: COC1OC(COC2OCC(OC(C)=O)C(O)C2OC2OC(COC(C)=O)C(O)C(O)C2OC(C)=O)C(O)C(O)C1OC1OCC(O)C(O)C1O]
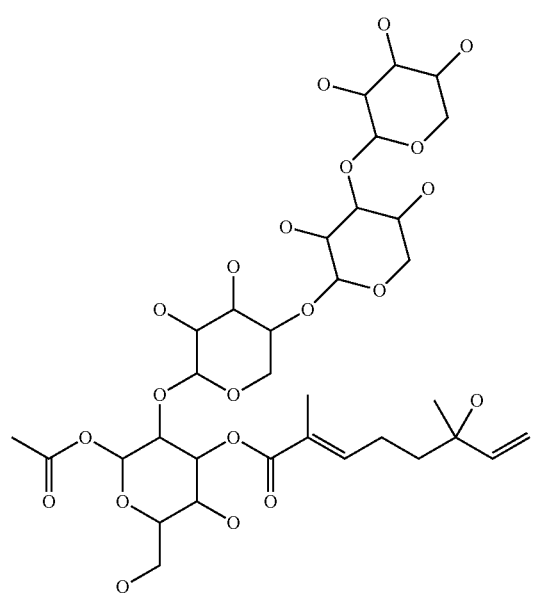 [SMILES: C=CC(C)(O)CC/C=C(\C)C(=O)OC1C(O)C(CO)OC(OC(C)=O)C1OC1OCC(OC2OCC(O)C(OC3OCC(O)C(O)C3O)C2O)C(O)C1O]
A20
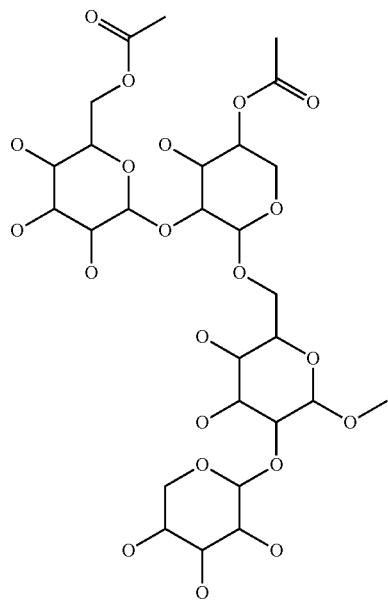 [SMILES: COC1OC(COC2OCC(OC(C)=O)C(O)C2OC2OC(COC(C)=O)C(O)C(O)C2O)C(O)C(O)C1OC1OCC(O)C(O)C1O]
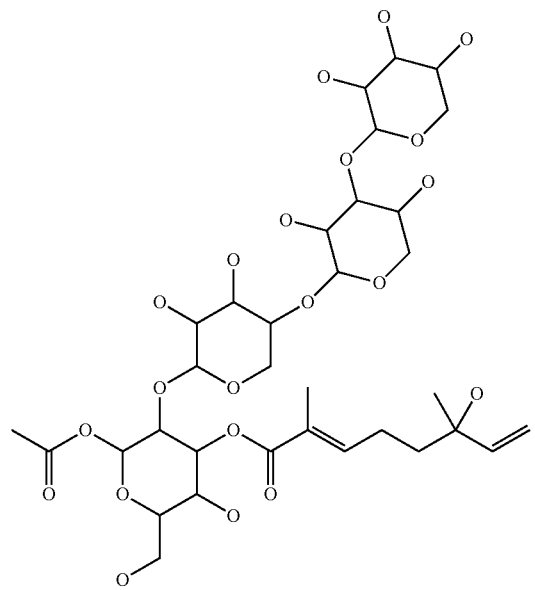 [SMILES: C=CC(C)(O)CC/C=C(\C)C(=O)OC1C(O)C(CO)OC(OC(C)=O)C1OC1OCC(OC2OCC(O)C(OC3OCC(O)C(O)C3O)C2O)C(O)C1O]

TABLE 1-continued
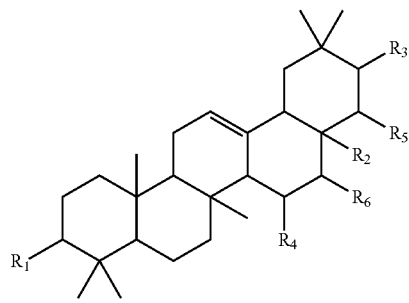
(I)
| | | |
|---|---|---|
| A21 | —O-glc-pyr-pyr | 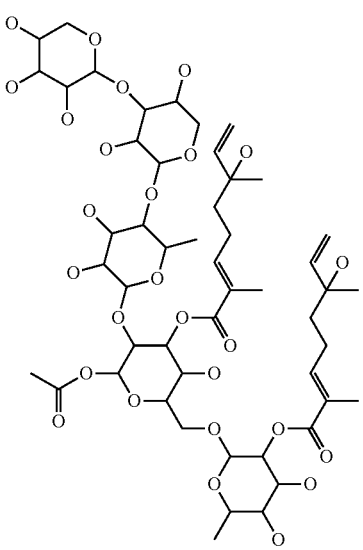 |
| A22 | —O-pyr-glc | —CH$_2$OH |
| A23 | —O-glc-glc-pyr | —CO$_2$-pyr-glc-glc-rha |
| A24 | 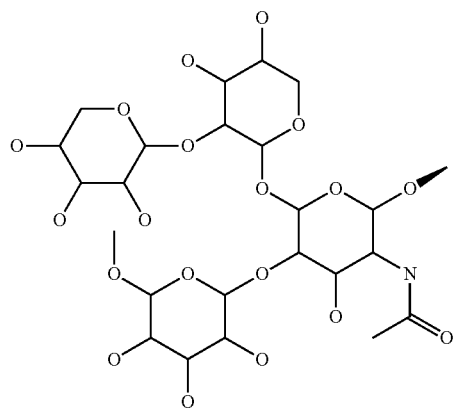 | 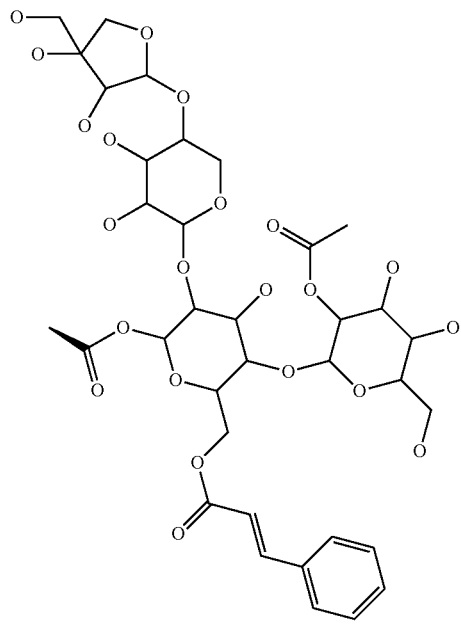 |

TABLE 1-continued
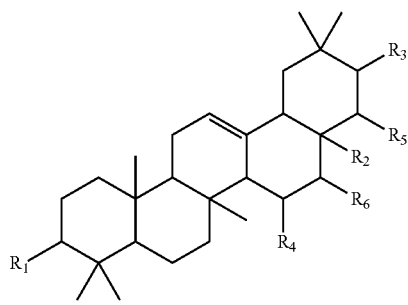
(I)
| A25 | —O-glc-pyr-pyr | 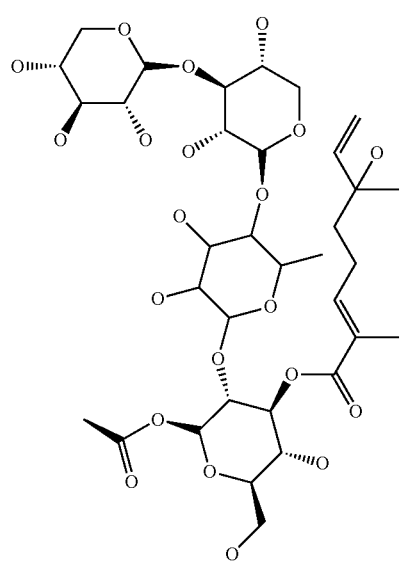 |
| A26 | —O-glc-pyr-pyr | 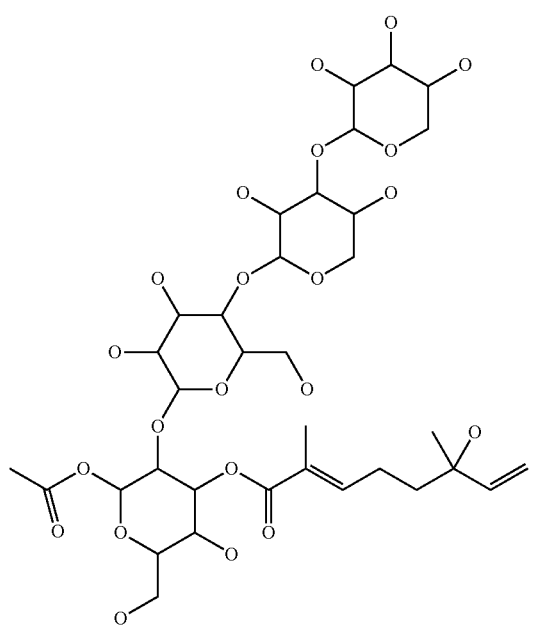 |
| A27 | —O-glc-glc-pyr | —CO$_2$-pyr-glc-glc-rha |

TABLE 2

| No. | $CC_{15}$ (μM) | $CC_{50}$ (μM) | Compound concentration (μM) | Inhibition rate (%) | $IC_{50}$ (μM) | EW ($CC_{50}/IC_{50}$) |
|---|---|---|---|---|---|---|
| A01 | >100 | >100 | 10 | 41.5 ± 26.7 | — | — |
| A02 | 2.9 | 15.2 | 10 | 96.7 ± 0.6 | 0.34 ± 0.06 | 44.71 |
| A03 | 12.7 | 23.1 | 10 | 13.3 ± 8 | — | — |
| A04 | >100 | >100 | 10 | 3.1 ± 12.9 | — | — |
| A05 | 16.1 | 23.2 | 10 | 50 ± 11.6 | — | — |
| A06 | 8.9 | 25.2 | 8 | 94.7 ± 1.1 | 0.010 ± 0.004 | 2520 |
| A07 | >100 | >100 | 10 | 10.3 ± 11.7 | — | — |
| A08 | 9.6 | 72.0 | 10 | 0.4 ± 22 | — | — |
| A09 | 3.1 | 26.1 | 10 | 13.6 ± 0.5 | — | — |
| A10 | 2.2 | 39.1 | 2 | 95.7 ± 0.6 | 0.31 ± 0.04 | 126.13 |
| A11 | 6.1 | 29.8 | 5 | 28.3 ± 9.1 | — | — |
| A12 | >100 | >100 | 10 | 95.8 ± 1 | 0.08 ± 0.003 | 1250 |
| A13 | 16.1 | 100.0 | 15 | 93.0 ± 0.3 | 3.31 ± 0.29 | 30.21 |
| A14 | 5.9 | >100 | 5 | 89.3 ± 0.8 | 1.95 ± 0.12 | 51.28 |
| A15 | >100 | >100 | 10 | 92 ± 1.6 | 3.94 ± 0.13 | 25.38 |
| A16 | 12.09 | 45.32 | 10 | 95.3 ± 0.3 | 0.42 ± 0.21 | 107.9 |
| A17 | 1.49 | 18.12 | 1 | 94.9 ± 1.2 | 0.057 ± 0.003 | 317.89 |
| A18 | 7.18 | 94.76 | 10 | 45 ± 2.9 | — | — |
| A19 | 1.17 | 17.86 | 1 | 94.8 ± 1.6 | 0.041 ± 0.005 | 435.61 |
| A20 | 18.85 | 50.17 | 10 | 96 ± 1.5 | 0.087 ± 0.01 | 576.67 |
| A21 | 11.64 | 56.72 | 10 | 97.3 ± 1.1 | 0.63 ± 0.07 | 90.03 |
| A22 | 8.62 | 40.01 | 10 | −0.8 ± 5.7 | — | — |
| A23 | 7.96 | 38.12 | 5 | 93.5 ± 0.4 | 0.23 ± 0.02 | 156.73 |
| A24 | 4.53 | 14.12 | 4 | 54.8 ± 5.4 | — | — |
| A25 | 10.29 | 64.11 | 10 | 96.5 ± 0.8 | 0.36 ± 0.016 | 178.08 |
| A26 | 7.94 | 38.36 | 10 | 95.6 ± 1.2 | 0.45 ± 0.04 | 85.24 |
| A27 | 19.44 | 76.72 | 10 | 96.9 ± 0.6 | 0.72 ± 0.07 | 106.56 |

$CC_{50}$: the concentration of the compound required to 50% cell kill (cytotoxicity).
$CC_{15}$: the concentration of the compound required to 15% cell kill (cytotoxicity).
$IC_{50}$: the concentration of the compound required to 50% inhibition of the HCV replication.
EW: the ratio of $CC_{50}/IC_{50}$.

In one embodiment, the disclosure provides a method for preventing or treating hepatitis C in a subject in need thereof, comprising administering the subject the pharmaceutical composition given above. The administration may be individual or combined with other drugs. The route of administration is not specifically limited and can be oral, transdermal, intraperitoneal, intravenous, nasal or intravitreal, but oral administration is preferable. The regime can be appropriately adjusted according to the conventional routines practiced by the practitioners in the art. The subject may comprise mammals, like rodents, pigs, cattle, sheep, goats, rabbits, dogs, cats, chickens, monkeys, primates or human. The dosage of the administration is not specifically limited and can be determined by the practitioners according to a patient's age, weight, health condition, disease type, disease development, affected parts, etc.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for treating hepatitis C in a subject in need thereof, comprising administering the subject a pharmaceutical composition comprising a compound represented by the following formula or a stereoisomer thereof as an active ingredient:

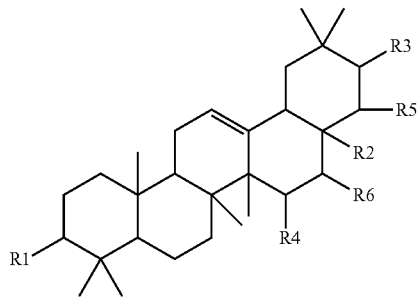

wherein $R_1$ represents an oxy group bonded with 1~5 unsubstituted or substituted pentose, hexose or a combination thereof; $R_2$ represents a hydroxymethyl group or a carbonyl group bonded with 1~5 unsubstituted or substituted pentose, hexose or a combination thereof; $R_3$ represents a hydrogen atom, hydroxyl, $C_1$~$C_{12}$ alkylcarbonyloxy, $C_2$~$C_{12}$ alkenylcarbonyloxy or saccharide group substituted with $C_1$~$C_{12}$ alkylcarbonyloxy or $C_2$~$C_{12}$ alkenylcarbonyloxy; $R_4$ represents a hydrogen atom, hydroxyl, $C_1$~$C_{12}$ alkylcarbonyloxy or $C_2$~$C_{12}$ alkenylcarbonyloxy group; $R_5$ represents a hydrogen atom, hydroxyl, $C_1$~$C_{12}$ alkylcarbonyloxy, $C_2$~$C_{12}$ alkenylcarbonyloxy or phenylcarbonyloxy group; and $R_6$ represents a hydrogen atom, hydroxyl or $C_1$~$C_{12}$ alkylcarbonyloxy group.

2. The method as claimed in claim 1, wherein $R_4$ represents a $C_2$~$C_{12}$ alkenylcarbonyloxy group.

3. The method as claimed in claim 1, wherein $R_1$ represents an oxy group bonded with one unsubstituted or substituted glucose and one unsubstituted or substituted pyranose, and $R_2$ represents a carbonyl group bonded with two unsubstituted or substituted pyranoses and one unsubstituted or substituted rhamnose.

4. The method as claimed in claim 1, wherein $R_1$ represents an oxy group bonded with two unsubstituted or substituted glucoses and three unsubstituted or substituted pyranoses, and $R_2$ represents a carbonyl group bonded with one unsubstituted or substituted glucose, one unsubstituted or substituted pyranose and one unsubstituted or substituted furanose.

5. The method as claimed in claim 1, wherein $R_1$ represents an oxy group bonded with two unsubstituted or substituted glucoses and one unsubstituted or substituted pyranose, and $R_2$ represents a carbonyl group bonded with two unsubstituted or substituted glucoses and three unsubstituted or substituted pyranoses.

6. The method as claimed in claim 1, wherein $R_1$ represents an oxy group bonded with one unsubstituted or substituted glucose and one unsubstituted or substituted pyranose, and $R_2$ represents a carbonyl group bonded with two unsubstituted or substituted rhamnoses and one unsubstituted or substituted pyranose.

7. The method as claimed in claim 1, wherein $R_1$ represents an oxy group bonded with one unsubstituted or substituted rhamnose, one unsubstituted or substituted pyranose and two unsubstituted or substituted glucoses, and $R_2$ represents a hydroxymethyl group.

8. The method as claimed in claim 1, wherein $R_1$ represents an oxy group bonded with one unsubstituted or substituted rhamnose, one unsubstituted or substituted pyranose and two unsubstituted or substituted glucoses, $R_2$ represents a hydroxymethyl group, and $R_4$ represents an alkenylcarbonyloxy group.

9. The method as claimed in claim 1, wherein $R_1$ represents an oxy group bonded with two unsubstituted or substituted pyranoses and two unsubstituted or substituted glucoses, and $R_2$ represents a carbonyl group bonded with one unsubstituted or substituted furanose, one unsubstituted or substituted pyranose and two unsubstituted or substituted glucoses.

10. The method as claimed in claim 1, wherein $R_1$ represents an oxy group bonded with two unsubstituted or substituted pyranoses and two unsubstituted or substituted glucoses, and $R_2$ represents a carbonyl group bonded with three unsubstituted or substituted pyranoses and one unsubstituted or substituted glucose.

11. The method as claimed in claim 1, wherein $R_1$ represents an oxy group bonded with two unsubstituted or substituted pyranoses and one unsubstituted or substituted glucose, and $R_2$ represents a carbonyl group bonded with two unsubstituted or substituted pyranoses, one unsubstituted or substituted glucose and two unsubstituted or substituted rhamnoses.

12. The method as claimed in claim 1, wherein $R_1$ represents an oxy group bonded with one unsubstituted or substituted pyranose and two unsubstituted or substituted glucoses, and $R_2$ represents a carbonyl group bonded with one unsubstituted or substituted pyranose, two unsubstituted or substituted glucoses and one unsubstituted or substituted rhamnose.

13. The method as claimed in claim 1, wherein $R_1$ represents an oxy group bonded with two unsubstituted or substituted pyranoses and one unsubstituted or substituted glucose, and $R_2$ represents a carbonyl group bonded with two unsubstituted or substituted pyranoses, one unsubstituted or substituted glucose and one unsubstituted or substituted rhamnose.

14. The method as claimed in claim 1, wherein $R_1$ represents an oxy group bonded with two unsubstituted or substituted pyranoses and one unsubstituted or substituted glucose, and $R_2$ represents a carbonyl group bonded with two unsubstituted or substituted pyranoses and two unsubstituted or substituted glucoses.

15. The method as claimed in claim 1, wherein R1 represents an oxy group bonded with one unsubstituted or substituted pyranose and two unsubstituted or substituted glucoses, and R2 represents an carbonyl group bonded with one unsubstituted or substituted pyranose, two unsubstituted or substituted glucoses and one unsubstituted or substituted rhamnose.

16. A method for treating hepatitis C in a subject in need thereof, comprising administering the subject a pharmaceutical composition comprising a compound as an active ingredient, wherein the compound comprises at least one compound selected from a group consisting of the following Formulae (A2), (A6), (A10), (A12), (A13), (A14), (A15), (A16), (A17), (A19), (A20), (A21), (A23), (A25), (A26) and (A27), and a salt thereof or a stereoisomer thereof,

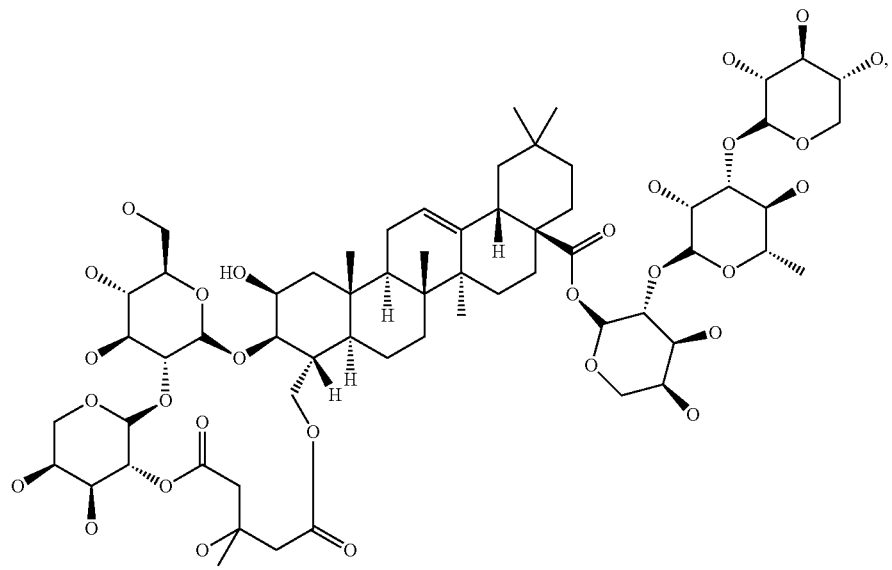

(A2)

-continued
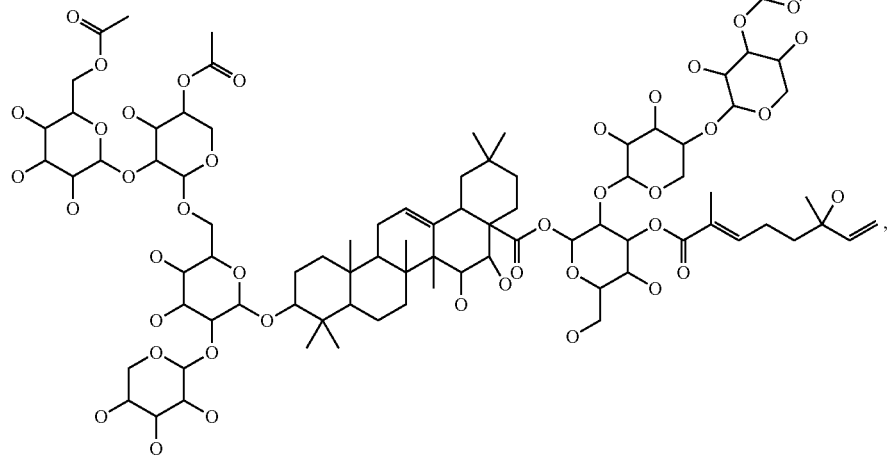
(A20)
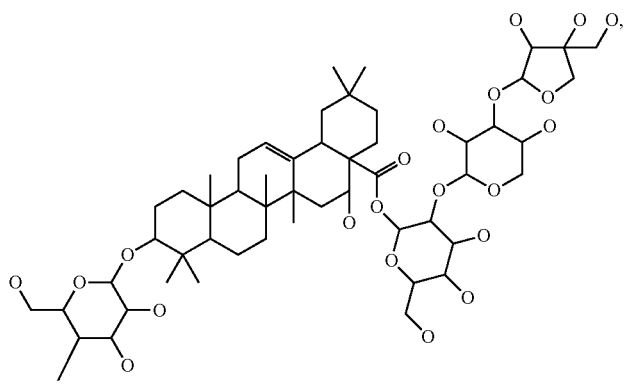
(A6)
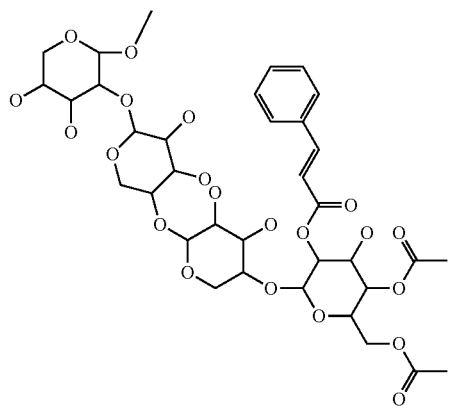

-continued
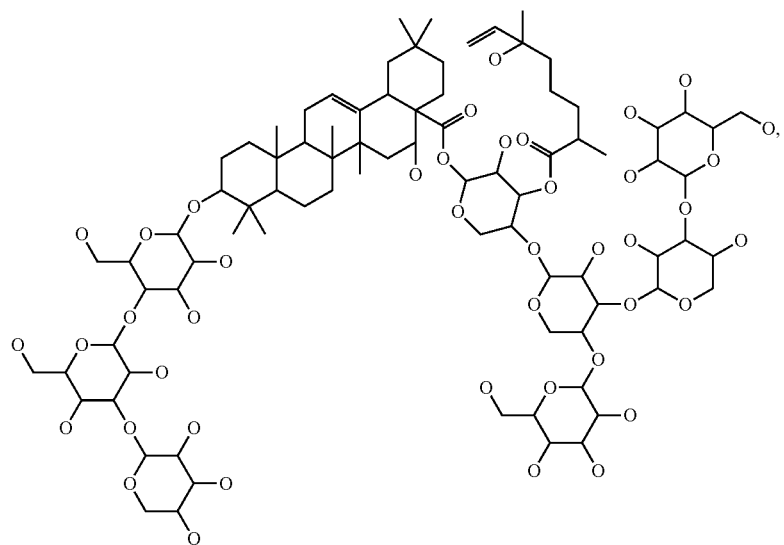
(A10)
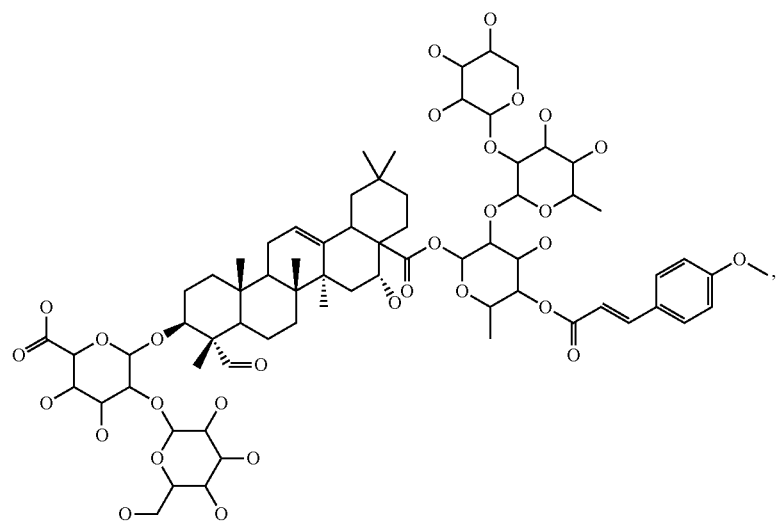
(A12)

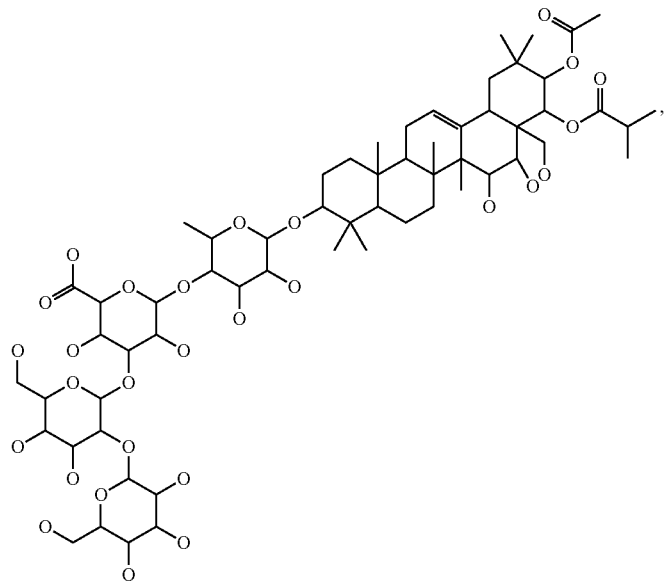
(A13)
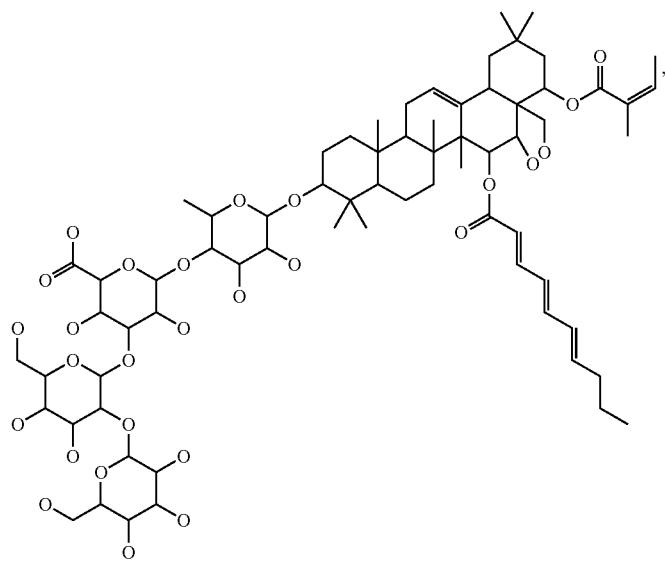
(A14)

-continued
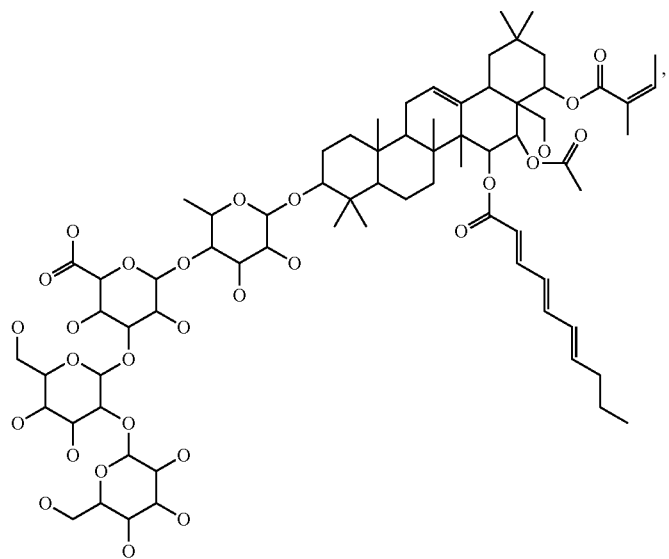
(A15)
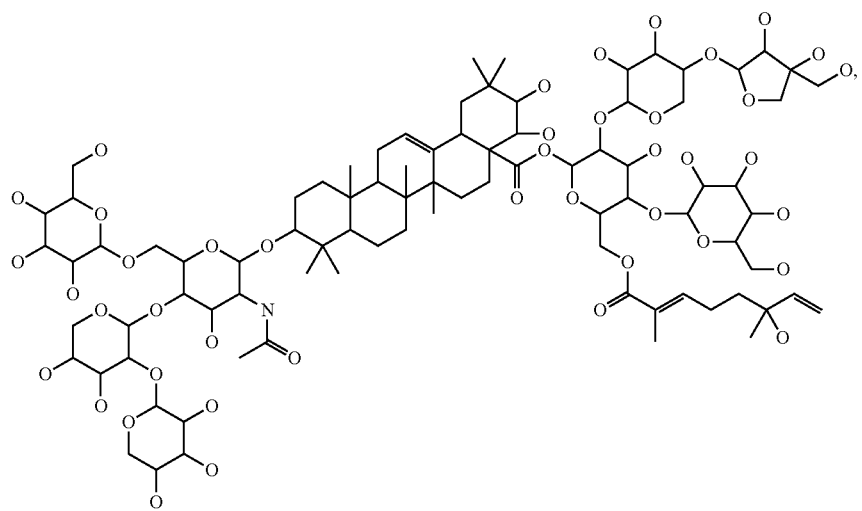
(A16)
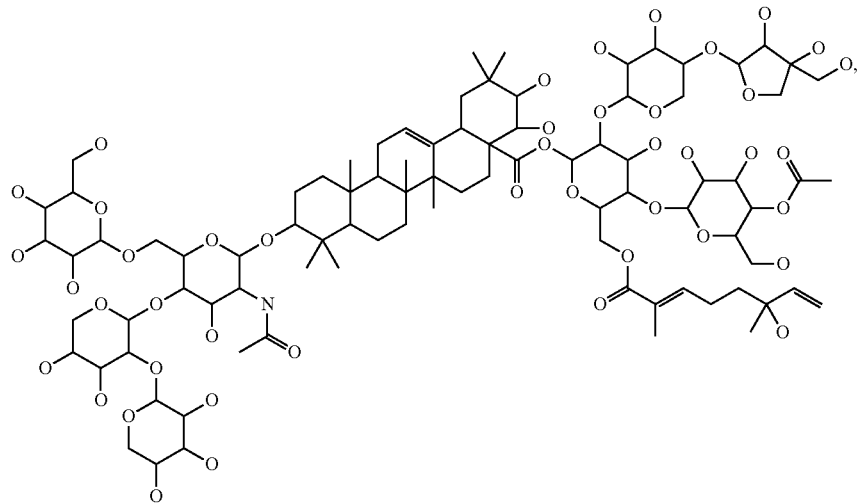
(A17)

-continued
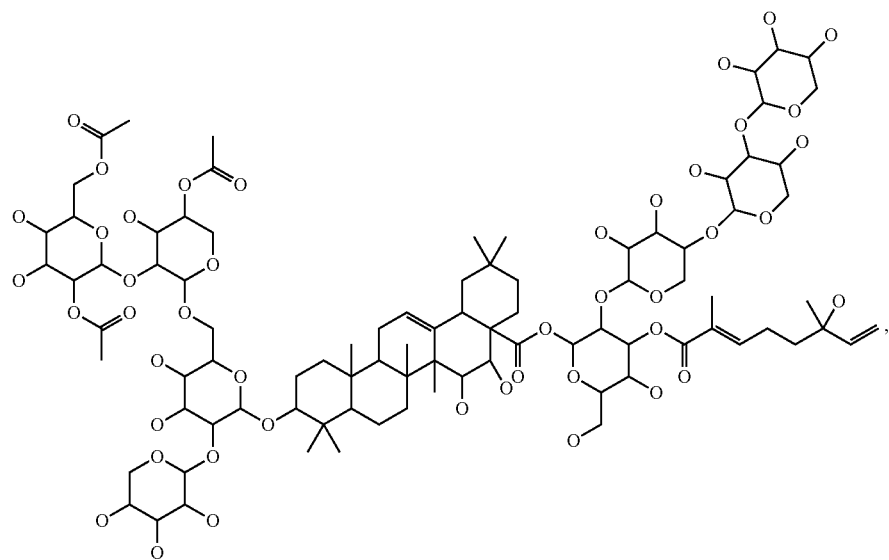
(A19)
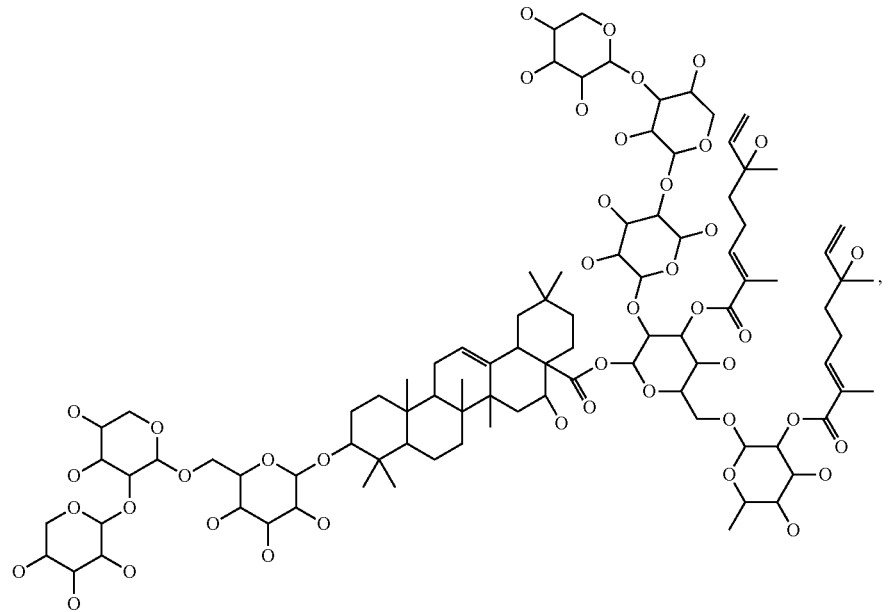
(A21)

-continued
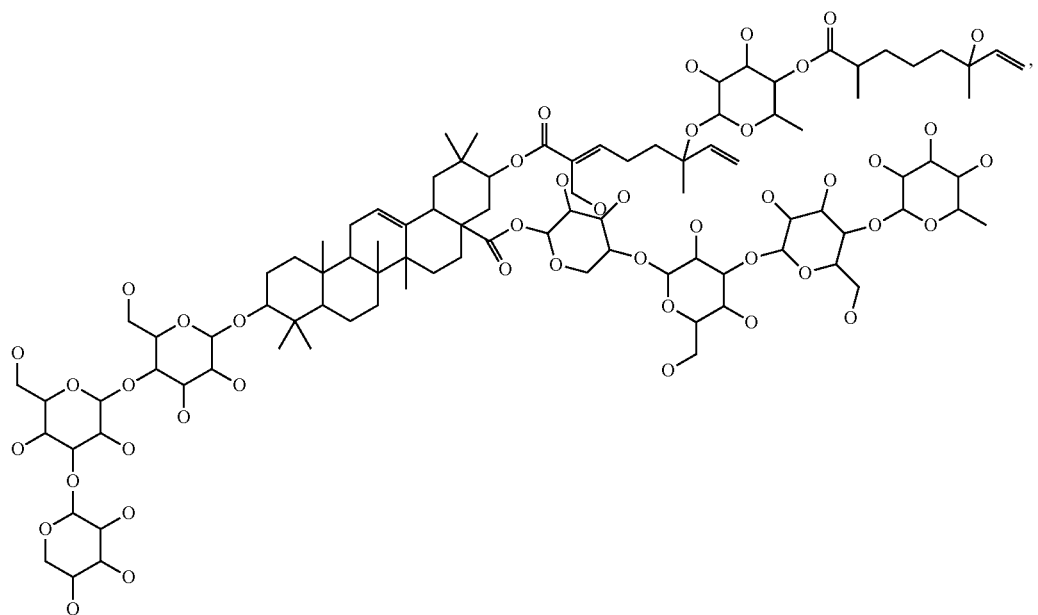
(A23)
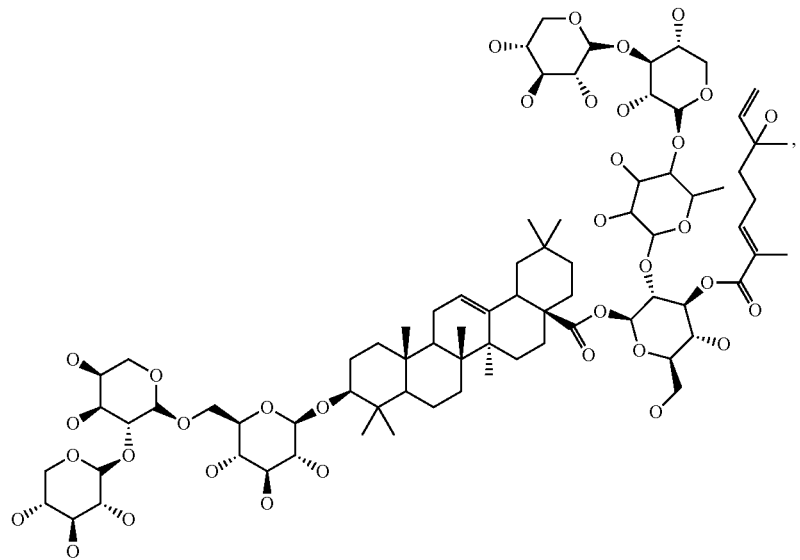
(A25)

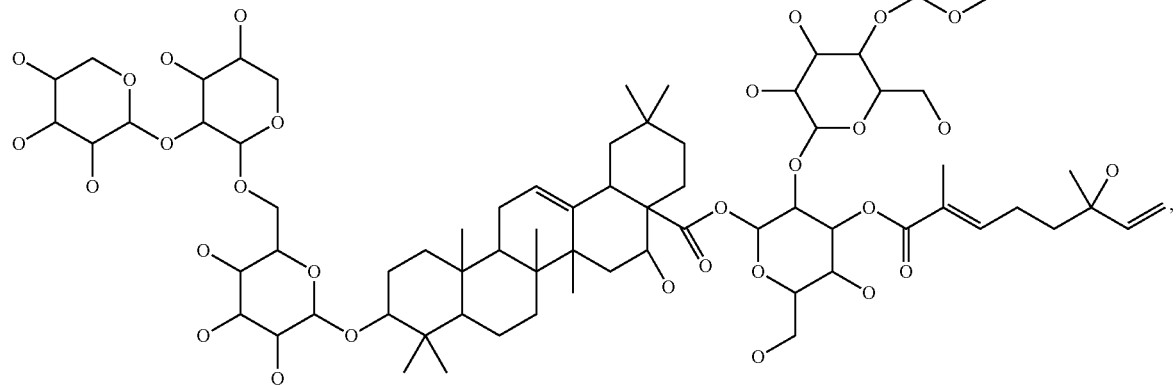
(A26)
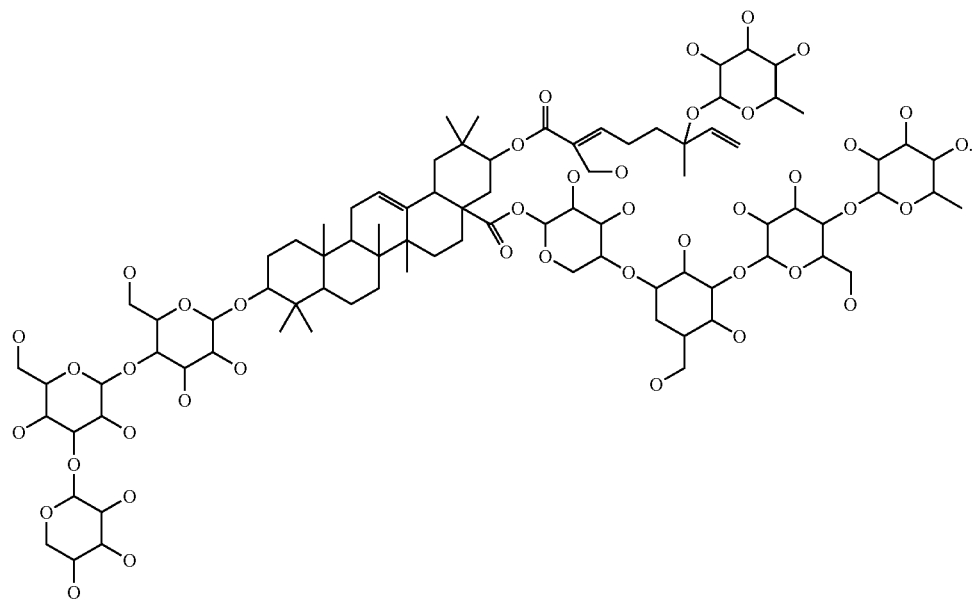
(A27)
* * * * *